(12) United States Patent
Anderson et al.

(10) Patent No.: US 12,070,345 B2
(45) Date of Patent: Aug. 27, 2024

(54) SYSTEMS AND METHODS FOR DISPLAYING IMAGES TO PATIENT RESIDING ON MOVABLE TABLE DURING MEDICAL IMAGING OR THERAPEUTIC PROCEDURES

(71) Applicant: INNOVERE MEDICAL INC., Markham (CA)

(72) Inventors: Kevan James Thompson Anderson, Cobourg (CA); Garry Ka Chun Liu, Etobicoke (CA); David Robert Green, Toronto (CA); Lynsie Alexandra Marie Thomason, Toronto (CA); Donald Bruce Plewes, Toronto (CA)

(73) Assignee: INNOVERE MEDICAL INC., Markham (CA)

( * ) Notice: Subject to any disclaimer, the term of this patent is extended or adjusted under 35 U.S.C. 154(b) by 0 days.

(21) Appl. No.: 18/106,309

(22) Filed: Feb. 6, 2023

(65) Prior Publication Data
US 2023/0329655 A1    Oct. 19, 2023

Related U.S. Application Data

(63) Continuation of application No. 16/753,082, filed as application No. PCT/CA2018/051242 on Oct. 2, 2018, now Pat. No. 11,571,174.

(Continued)

(51) Int. Cl.
*A61B 6/00*          (2024.01)
*A61B 6/03*          (2006.01)
(Continued)

(52) U.S. Cl.
CPC .............. *A61B 6/462* (2013.01); *A61B 6/032* (2013.01); *A61B 6/037* (2013.01); *A61B 6/0407* (2013.01);
(Continued)

(58) Field of Classification Search
CPC ..... A61B 5/055; A61B 5/1113; A61B 5/1128; A61B 5/704; A61B 5/742; A61B 5/744;
(Continued)

(56) References Cited

U.S. PATENT DOCUMENTS 11,571,174 B2*   2/2023   Anderson .............. A61B 5/055
2017/0119320 A1*   5/2017   Ueda ........................ A61B 5/11

* cited by examiner

*Primary Examiner* — Dani Fox
(74) *Attorney, Agent, or Firm* — HILL & SCHUMACHER

(57) ABSTRACT

Systems and methods are provided for delivering images to a patient before and/or during a medical procedure in which a patient is translated on a table relative to a gantry. In various example embodiments, images are projected to the patient while preserving the projected field size during table motion, thereby potentially reducing patient anxiety by providing a more immersive patient viewing experience. In some embodiments, the projected field size is maintained by a display system that is secured to the table such that both a projector and a projection screen are fixed relative to the table, and relative to the patient, during translation of the table. In some example embodiments, a reduction in patient anxiety may be achieved by projecting images as virtual images that are perceived by the patient as residing at a depth that lies beyond the confined spatial region in which the patient resides.

21 Claims, 18 Drawing Sheets

Related U.S. Application Data

(60) Provisional application No. 62/567,053, filed on Oct. 2, 2017.

(51) Int. Cl.
*A61B 6/04* (2006.01)
*A61B 6/46* (2024.01)
*G01R 33/28* (2006.01)

(52) U.S. Cl.
CPC ............ *A61B 6/4435* (2013.01); *A61B 6/547* (2013.01); *G01R 33/283* (2013.01)

(58) Field of Classification Search
CPC ....... A61B 6/032; A61B 6/037; A61B 6/0407; A61B 6/4435; A61B 6/462; A61B 6/547; A61B 90/36; A61N 5/0618; A61N 5/10
See application file for complete search history.

US 12,070,345 B2

SYSTEMS AND METHODS FOR DISPLAYING IMAGES TO PATIENT RESIDING ON MOVABLE TABLE DURING MEDICAL IMAGING OR THERAPEUTIC PROCEDURES

CROSS-REFERENCE TO RELATED APPLICATION

This application is a National Phase application claiming the benefit of the international PCT Patent Application No. PCT/CA2018/051242, filed on Oct. 2, 2018, in English, which claims priority to U.S. Provisional Application No. 62/567,053, titled "SYSTEMS AND METHODS FOR DISPLAYING IMAGES TO PATIENT RESIDING ON MOVABLE TABLE DURING MEDICAL IMAGING OR THERAPEUTIC PROCEDURES" and filed on Oct. 2, 2017, the entire contents of which are incorporated herein by reference.

BACKGROUND

The present disclosure relates to gantry-based medical imaging systems and medical therapeutic systems. More particularly, the present disclosure relates to patient entertainment and communication systems for use with gantry-based medical imaging and therapeutic systems.

Many medical imaging and therapeutic systems, such as magnetic resonance imaging systems and radiation treatment systems, employ a configuration in which a medical imaging or therapeutic device is supported by a gantry. Such systems typically employ a positionable table (also commonly referred to as a couch) to facilitate the positioning of the patient relative to the gantry.

For example, prior to initiating a magnetic resonance imaging scan, a patient is typically instructed to lie on the table and the table is then translated such that at least a portion of the patient is moved into the bore of the magnetic resonance imaging gantry. Given the narrow diameter of the gantry bore and the loud noise of the scanner, the experience of being drawn into the bore and held within the bore during scanning results in significant claustrophobia and anxiety for the patient, in addition to any anxiety that a patient may already be experiencing due to health concerns.

SUMMARY

Systems and methods are provided for delivering images to a patient before and/or during a medical procedure in which a patient is translated on a table relative to a gantry. In various example embodiments, images are projected to the patient while preserving the projected field size during table motion, thereby potentially reducing patient anxiety by providing a more immersive patient viewing experience. In some example embodiments, the projected field size is maintained by a display system that is secured to the table such that both a projector and a projection screen are fixed relative to the table, and relative to the patient, during translation of the table. In some example embodiments, a reduction in patient anxiety may be achieved by projecting images as virtual images that are perceived by the patient as residing at a depth that lies beyond the confined spatial region in which the patient resides.

Accordingly, in a first aspect, there is provided a medical imaging and/or therapeutic system comprising:
a gantry supporting a medical imaging device or a medical therapeutic device;
a table translatable relative to the gantry;
a projector;
a projection screen, wherein the projection screen is positioned, relative to the projector, to provide a display surface for images projected by the projector; and
a mirror supported relative to the projection screen such that the images projected onto the projection screen are viewable through the mirror by a patient when the patient is residing on the table;
wherein the projector, the mirror and the projection screen are supported relative to the table such that they move in unison with the table while maintaining a fixed spatial relationship therebetween, and such that images projected by the projector onto the projection screen during translation of the table are projected with a constant projected image field size, thereby reducing a perception of motion by the patient as the patient is translated relative to the gantry.

In another aspect, there is provided a method of displaying images to a patient prior to or during a procedure involving a medical imaging and/or therapeutic system, the medical imaging and/or therapeutic system comprising:
a gantry supporting a medical imaging device or a medical therapeutic device;
a table translatable relative to the gantry;
a projector;
a projection screen, wherein the projection screen is positioned, relative to the projector, to provide a display surface for images projected by the projector; and
a mirror supported relative to the projection screen such that the images projected onto the projection screen are viewable through the mirror by the patient when the patient is residing on the table;
wherein at least the mirror and the projection screen are supported relative to the table such that they move in unison with the table while maintaining a fixed spatial relationship therebetween;
the method comprising:
during translation of the table relative to the gantry, controlling the projector to project the images onto the projection screen such that the images are projected with a constant projected image field size, thereby reducing a perception of motion by the patient as the patient is translated relative to the gantry.

In another aspect, there is provided a display system for use with a medical imaging and/or therapeutic system, the medical imaging and/or therapeutic system comprising a gantry and a table translatable relative to the gantry, the display system comprising:
one or more support frames, wherein each support frame is attachable to the table, such that each support frame moves in unison with the table when attached thereto;
a projector;
a projection screen, wherein the projection screen is positioned, relative to the projector, to provide a display surface for images projected by the projector;
a mirror, wherein the mirror is positioned relative to the projection screen such that the images projected onto the projection screen are viewable through the mirror by a patient residing on the table;
wherein the projector, the mirror and the projection screen are supportable relative to the table by the one or more support frames, such that when the one or more support frames are attached to the table, a fixed spatial relationship is maintained between the projector, the mirror and the projection screen during translation of the table relative to the gantry, such that images projected by the projector onto the projection screen during translation of the table are projected with a constant projected image field size, thereby reducing a perception of motion by the patient as the patient is translated relative to the gantry.

In another aspect, there is provided a medical imaging or medical therapeutic system comprising:
- a gantry supporting a medical imaging device or a medical therapeutic device;
- a table translatable relative to the gantry;
- a movable projector;
- a projection screen, wherein the projection screen is positioned to provide a display surface for images projected by the projector;
- a mirror supported relative to the projection screen such that the images projected onto the projection screen are viewable through the mirror by a patient when the patient is residing on the table;
- wherein the mirror and the projection screen are supported, relative to the table, such that they move in unison with the table while maintaining a fixed spatial relationship therebetween; and
- control circuitry for controlling a position of the movable projector such that images projected by the projector onto the projection screen during translation of the table are projected with a constant projected image field size, thereby reducing a perception of motion by the patient as the patient is translated relative to the gantry.

In another aspect, there is provided a medical imaging and/or therapeutic system comprising:
- a gantry supporting a medical imaging device or a medical therapeutic device;
- a table translatable relative to the gantry;
- a projector comprising a controllable optical imaging assembly for controlling a projected image size of projected images;
- a projection screen, wherein the projection screen is positioned to provide a display surface for the images projected by the projector;
- a mirror, wherein the mirror is positioned relative to the projection screen such that the images projected onto the projection screen are viewable through the mirror by the patient;
- wherein the mirror and the projection screen are supported relative to the table such that they move in unison with the table while maintaining a fixed spatial relationship therebetween
- control circuitry for controlling the controllable optical imaging assembly such that images projected by the projector onto the projection screen during translation of the table are projected with a constant projected image field size, thereby reducing a perception of motion by the patient as the patient is translated relative to the gantry.

In another aspect, there is provided a medical imaging and/or therapeutic system comprising:
- a gantry supporting a medical imaging device or a medical therapeutic device;
- a table translatable relative to the gantry;
- a display device positioned such that the display device is visible to a patient when the patient resides on the table;
- a lens supported such that the display device is visible to the patient through the lens, wherein the lens is configured such that a magnified virtual image of the display device is perceived by the patient;
- wherein the display device and the lens are supported relative to the table such that they move in unison with the table while maintaining a fixed spatial relationship therebetween, such that images displayed by the display device during translation of the table are displayed with a constant projected image field size, thereby reducing a perception of motion by the patient as the patient is translated relative to the gantry.

In another aspect, there is provided a medical imaging and/or therapeutic system comprising:
- a gantry supporting a medical imaging device or a medical therapeutic device;
- a table translatable relative to the gantry;
- a display screen supported such that the display screen is visible to a patient when the patient resides on the table;
- an optical focusing element supported such that the display screen is visible to the patient via transmission through the optical focusing element or reflection from the optical focusing element, wherein the optical focusing element is configured such that a magnified virtual image of the display screen is perceived by the patient;
- wherein the display screen and the optical focusing element are supported relative to the table such that they move in unison with the table while maintaining a fixed spatial relationship therebetween, such that images displayed by the display screen during translation of the table are displayed with a constant projected image field size, thereby reducing a perception of motion by the patient as the patient is translated relative to the gantry.

In another aspect, there is provided a medical imaging and/or therapeutic system comprising:
- a gantry supporting a medical imaging device or a medical therapeutic device;
- an optical subsystem for displaying images to a patient during a medical procedure;
- wherein the optical subsystem is configured such that a magnified virtual image is perceived by the patient at a depth that extends beyond an overhead inner surface of the gantry.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 11A, 11B, 11C, 110, 11E, 11F, 11G, 11H, 11I and 11J show various example embodiments in which one or more motion tracking cameras are integrated with a display system for displaying images to a patient while tracking the motion of the patient's head.

DETAILED DESCRIPTION

Figure 1A:
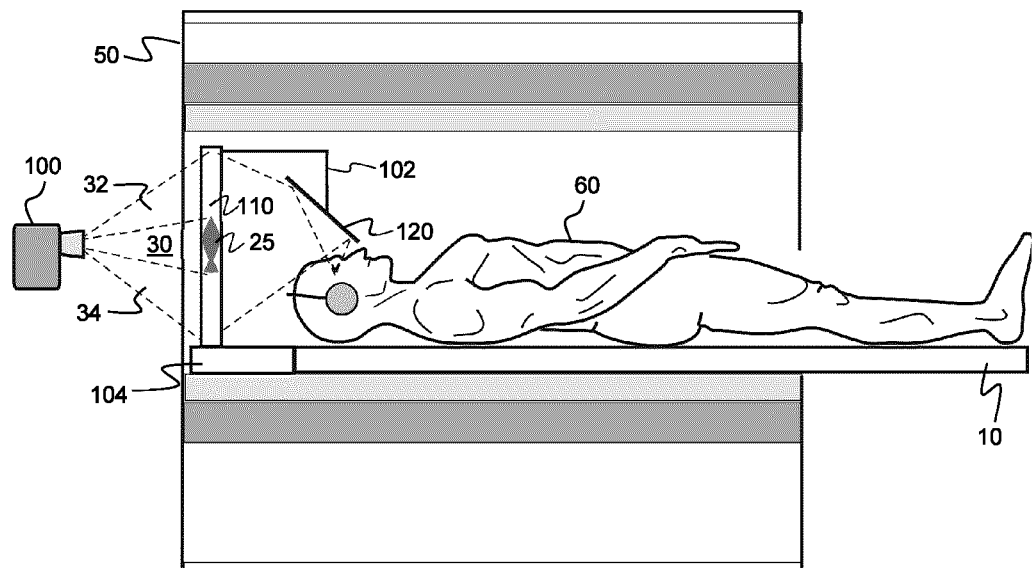
FIGS. 1A and 1B illustrate an example of a magnetic resonance imaging system for displaying images to a patient within the scanner bore.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Various example embodiments of the present disclosure provide systems, methods and devices for delivering media content, such as images and video, to a patient during a medical procedure involving a gantry-based medical imaging or therapeutic system. Many of the example embodiments of the present disclosure may be beneficially employed to reduce patient anxiety prior to and/or during a medical procedure by delivering images to the patient that reduce the patient's sense of confinement.

A step towards this goal of reducing confinement-associated patient anxiety during imaging procedures was recently taken by Ohmure et al. in US Patent Publication No. 2017/0123020, which disclosed a gantry-based medical image diagnosis system configured to project images into the bore of a gantry when the patient is horizontally translated on the table. According to the teachings of Ohmure et al., a fixed external projector is employed to project images onto a movable screen unit that is slidably movable along rails of the gantry. The movable screen unit, supported by the gantry rails, is connected in a serial fashion to an end of the table, such that the movable screen translates horizontally in unison with the table.

FIG. 1A illustrates an example of the configuration taught by Ohmure et al. A patient 60 is shown residing in a table 10 within a bore of a magnetic resonance imaging gantry 50. A projector 100, residing at a fixed location beyond the magnetic resonance imaging gantry 50, projects images into the bore of the gantry 50, and the images are projected onto a projection screen 110 that is supported by a base 104. The patient 60 views the projection screen 110 through a viewing mirror 120. The viewing mirror 120 is supported, relative to the projection screen 110, by a support arm 102. Ohmure et al. teaches that a benefit of the design shown in FIG. 1A is that as the table 10 is moved relative to the gantry, the distance between the patient 60 and the projection screen 110 is fixed, thereby maintaining a sense of immersion in the images by the patient, and reducing the "locked up" feeling when the patient is drawn into the bore of the gantry 50.

The present inventors have found that the design of Ohmure et al., while facilitating some degree of patient immersion in the images, does not produce a full sense of immersion in the image due to changes in the projected image that occur when the table is moved relative to the gantry. The effect of changes in the table position on the image size can be seen by comparing the projected images in FIG. 1A to those projected in FIG. 1B. In FIG. 1A, the table 10 is located such that patient resides deep within the bore of the gantry 50, and the projected field from the projector fills the projection screen 110. The projected field is shown as having an inner region 30 (in which in image of a fish 25 is projected, and outer regions 32 and 34.

Figure 1B:
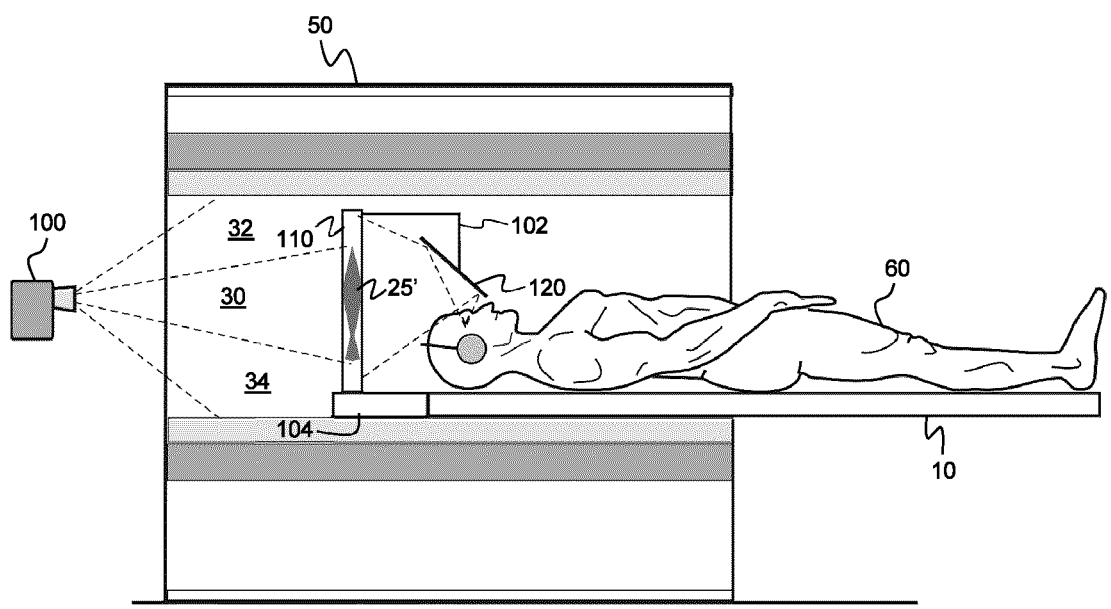

FIG. 1B shows how a change in the location of the table 10 can impact the images that are viewed by the patient 60. With the table 10 partially extending from the bore of the gantry 50, the projection screen 110 is now located further away from the projector 100. As a result of this longer separation between the projection screen 110 and the projector 100, the projected field at the screen location is now significantly larger than in FIG. 1A, and the projected field overfills the projection screen 110, spilling out into the inner walls of the gantry 50. This effect is clearly seen by comparing the regions 30, 32 and 34 in FIG. 1A and FIG. 1B. In FIG. 1A, all field regions are projected onto the projection screen 110. However, in FIG. 1B, only the inner region 30 fills the projection screen 110, and the outer field regions 32 and 34 are projected onto the inner walls of the gantry 50 due to the increased projected field size. This position-dependent overfilling of the projection screen can result in significant image distortion that is perceived by the patient, further reducing the immersive effect of the projected images.

As shown in FIGS. 1A and 1B, the changes in the size of the projected field are perceived by the patient 60 as causing the image to be magnified with a magnification factor that is dependent on distance. For example, a fish 25 that is shown in the projected image of FIG. 1A is magnified in the projected image of the fish 25' that is shown in FIG. 1B. This position dependence of the size of the projected images can lessen the immersive effect of the images.

In addition to changes in the perceived image size, changes in the table position, and the associated changes in the distance between the projector 100 and the projection screen 110, may cause noticeable changes in image sharpness. Indeed, as the projection screen 110 is moved away from a region of high focus, the clarify of the images that are projected onto the projection screen 110 will decrease.

It is therefore evident that changes in the position of the table 10 can result in several changes in the image that is viewed by the patient. These changes include (i) changes in image magnification, (ii) changes in image focus (sharpness or clarity), and (iii) changes in the relative amount of the image that is projected onto the inner wall of the gantry 50. Since these changes in the image properties are correlated with changes in table position, the perception of these changes may reduce the immersive effect of the images. For example, the changes in the image may heighten a sense of motion when the table is moved, and this sense of motion may result in heighten awareness of the patient that they are being moved into the gantry. The aforementioned drawbacks of the Ohmure system can limit the type of media that is presentable to the patient. For example, any media that has a recognizable measure of scale may be problematic due to the image magnification and demagnification effects that result from table motion. Since most forms of entertainment media (movies, television shows, video clips) and user interfaces (internet browser, media browsers) involve images that have very clear measures of scale—such as objects, text, people, scenery, and the image frame itself, such media may be problematic for a display system such as the Ohmure system.

Figure 2:
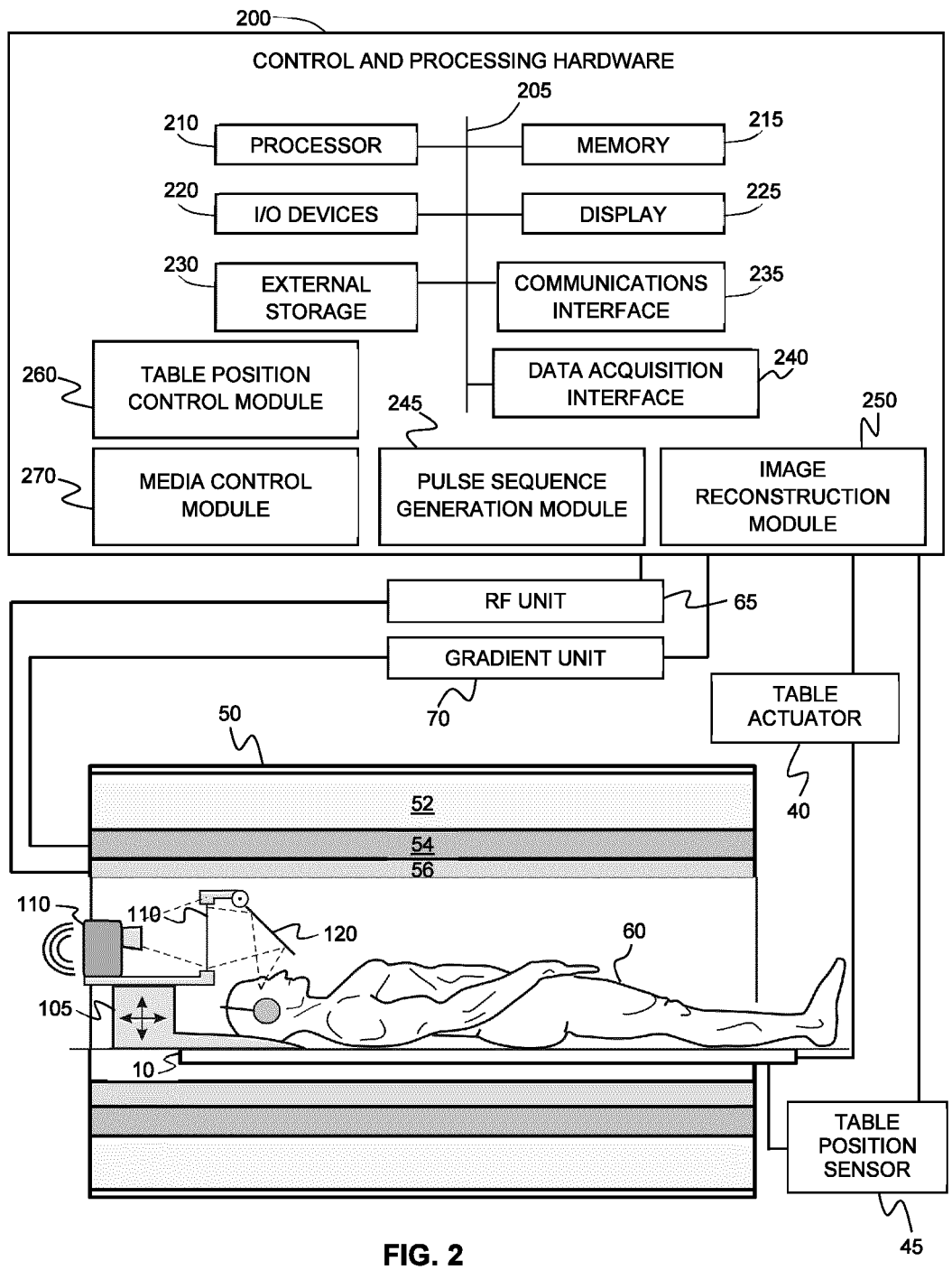
FIG. 2 shows an example of a magnetic resonance imaging system that is adapted to display images to a patient within the scanner bore with reduced sensitivity to table motion.

The present inventors set out to develop an image projection solution that would avoid the aforementioned problems associated with the Ohmure system and provide a more immersive solution leading to improved patient satisfaction and reduced anxiety. Referring now to FIG. 2, an example improved system is illustrated for displaying images to a patient during a gantry-based medical imaging or therapeutic procedure, where the example system does not suffer from the position-dependent image size scaling that is inherent in the Ohmure system.

While the example embodiments of the present disclosure may be adapted to a wide range of gantry-based medical imaging and therapeutic systems, the example system shown in FIG. 2 includes a magnetic resonance scanner gantry 50 that employs a main magnet 52 to produce a main magnetic field B0, which generates a polarization in the patient 60. The example system includes gradient coils 54 for generating magnetic field gradients. A receive coil 56 detects RF signals from patient 60. The receive coil 56 can also be used as a transmission coil for the generation of radio frequency (RF) pulses. Alternatively, a body coil or head coil (not shown) may be employed to radiate and/or detect RF pulses. The RF pulses are generated by an RF unit 65, and the magnetic field gradients are generated by a gradient unit 70.

The patient 60 resides on a table 10 that is positionable relative to the gantry 50. The table 10 may be manually positionable, or controllably positionable through one or more actuation mechanisms, such as motors, represented in FIG. 2 by a table actuator 40. The position of the table may be detected via one or more sensors, such as encoding sensors, as shown in FIG. 2 by table position sensor 45.

The example system of FIG. 2 includes an example of a display system for displaying images to the patient 60 without causing position-dependent image scaling when the table 10 is translated. The example display system includes a projector 100 that is supported in a fixed position relative to the table 10, by a support frame 105, such that the projector 10 moves in unison with the table 10. The support frame 105 also supports a projection screen 110 onto which images are projected, such that the projection screen 110 is fixed relative to the projector 100 (and the table 10). The projection screen 110 may be formed, for example, from a translucent material that diffuses light, such as frosted glass or translucent plastic.

As described in further detail below, the support frame 105 may be connected to the top surface of the table, a distal lateral surface, or a combination of surfaces. In some example implementations, the support frame 105 may engage (slidably) with rails or other positioning mechanisms of the gantry 50. The support frame 105 may be permanently affixed to the table, or may be removably affixed (removably attachable) to the table. The support frame 105 may be connected to the table through different attachment configurations, including, but not limited to, via an adhesive, a friction fit, one or more fasteners, or a combination thereof. For example, as described below, the support frame 105 may be connected to the table 10 through an equipment rail provided on the table 10.

A viewing mirror 120 is placed such that the patient can view images projected onto the projection screen 110 through the viewing mirror 120. The viewing mirror 120 may be supported by the support frame 105 (support arm or link not shown in figure). It will be understood that the support frame 105 may be provided as two or more support frames as opposed to a single support frame, provided that the projector 100, the projection screen 110, and the viewing mirror 120 are supported in a mutually fixed relationship, and in a manner that is fixed relative to the table 10. In an alternative example implementation, the viewing mirror may be supported by a head coil by a head-supporting frame (e.g. a stereotactic frame or cushioned head support).

As shown in FIG. 2, the fixed spatial relationship between the projector 100, the projection screen 110, and the viewing mirror 120 relative to the table 10 results in projected images that are viewable by the patient during translation of the table 10 such that the projected images maintain a fixed projected field size during translation. The fixed spatial relationship also maintains focus of the projected image during translation of the table 10, and avoids position-dependent overfilling of the projection screen 110. The present example embodiment thus addresses the shortcomings of the Ohmure system and provides a more immersive viewing experience for the patient that is absent of (or delivers significantly reduced) perceptible position-dependent image artifacts.

In the example implementation shown in FIG. 2, the medical gantry is a magnetic resonance imaging gantry 50, and the projector 100 is magnetic resonance imaging compatible. Magnetic resonance compatibility can be achieved by avoiding the use of ferromagnetic materials and operating electronics in frequency ranges outside of the operating bandwidth of the magnetic resonance scanner. Electromagnetic shielding may also be employed to avoid or reduce electromagnetic interference. For example, large currents flowing through inductors may cause electromagnetic emissions. These emissions can be reduced by employing shielding around the inductors. In one example implementation, shielding be provided to achieve continuous shielding on a circuit board (i.e. shielding connected to the ground plane).

In some example implementations, magnetic resonance compatibility may be achieved by substituting conventional ferrite core inductors with alternative components, such as, but not limited to, ferrite-free inductors such as phenolic-core, polymer-core, ceramic-core, or carbonyl-core inductors.

In some example implementations, the projector may be battery powered or may be powered through an external power source. The projector may receive displayable content, such as movies, television, videos, and/or a user interface for selecting content to be displayed, via a wired connection, a wireless connector, or through media stored in internal memory.

It will be understood that the MR system can have additional units or components that are not shown for clarity, such as, but not limited to, additional control or input devices, and additional sensing devices, such as devices for cardiac and/or respiratory gating. Furthermore, the various units can be realized other than in the depicted separation of the individual units. It is possible that the different components are assembled into units or that different units are combined with one another. Various units (depicted as functional units) can be designed as hardware, software or a combination of hardware and software.

In the example system shown in FIG. 2, control and processing hardware 200 controls the MRI scanner to generate RF pulses according to a suitable pulse sequence. The control and processing hardware 200 may include, for example, one or more processors 210, memory 215, a system bus 205, one or more input/output devices 220, and a plurality of optional additional devices such as communications interface 235, data acquisition interface 240, display 225, and external storage 230. The control and processing hardware 200 is interfaced with the MRI scanner gantry 50 for controlling the acquisition of the received MRI signals. The control and processing hardware 200 acquires the received MRI signals from the RF unit 65 and processes the MRI signals according to the methods described herein in order to perform image reconstruction and generate MRI images.

The control and processing hardware 200 may be programmed with a set of instructions which when executed in the processor causes the system to perform one or more methods described in the present disclosure. For example, as shown in FIG. 2, control and processing hardware 200 may be programmed with instructions in the form of a set of executable image processing modules, such as, but not limited to, a pulse sequence generation module 245, an image reconstruction module 250, a table position control module 260, and a media control module 270.

The pulse sequence generation module 245 may be implemented using algorithms known to those skilled in the art for pulse sequence generation. During MRI scanning, RF data is received from the RF coils 56. The pulse sequence generation module 245 establishes the sequence of RF pulses and magnetic field gradients depending on the desired imaging sequence, MR signals responsively emitted by the patient and detected by the coils 56 are acquired. The image reconstruction module 245 processes the acquired MRI signals to perform image reconstruction and MRI image generation.

In some example embodiments, the control and processing hardware, or addition control circuitry, may be employed to control the position of the table relative to the gantry. For example, the table position may be controlled by the table position control module 260 the control and processing hardware 200 by sending signals to the table actuator 40. The table position may by controlled in a closed-loop manner based on feedback obtained from one or more table position sensors 45. It will be understood that table orientation (e.g. one or more table angles) may additionally or alternatively be controlled.

In some example embodiments, the control and processing hardware, or addition control circuitry, may be employed to deliver displayable image content (media content) to the projector 110. For example, the media control module 270 may be employed to control the delivery of media content to the projector 110, through a wired or wireless connection. The media control module 270 may be employed to facilitate connection to a remote media delivery service, such as a remote media streaming service, through a connection to the internet.

It is to be understood that the example system shown in FIG. 2 is illustrative of a non-limiting example embodiment, and is not intended to be limited to the components shown. For example, the system may include one or more additional processors and memory devices. Furthermore, one or more components of control and processing hardware 200 may be provided as an external component that is interfaced to a processing device.

Some aspects of the present disclosure can be embodied, at least in part, in software, which, when executed on a computing system, configures the computing system as a specialty-purpose computing system that is capable of performing the signal processing and noise reduction methods disclosed herein, or variations thereof. That is, the techniques can be carried out in a computer system or other data processing system in response to its processor, such as a microprocessor, CPU or GPU, executing sequences of instructions contained in a memory, such as ROM, volatile RAM, non-volatile memory, cache, magnetic and optical disks, cloud processors, or other remote storage devices. Further, the instructions can be downloaded into a computing device over a data network, such as in a form of a compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine-readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), network attached storage, cloud storage, among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

Figure 3A:
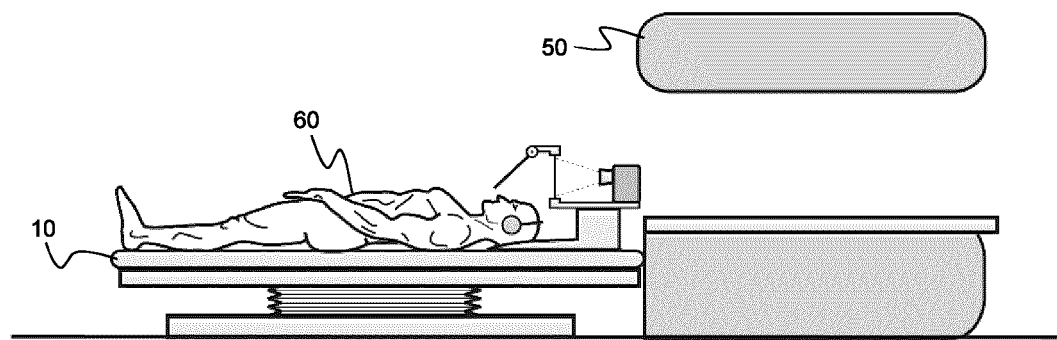
FIGS. 3A, 3B, and 3C illustrate an example embodiment in which a fixed spatial relationship between the projector, the projection screen, the viewing mirror, and the patient is maintained during motion of the table.
Figure 3B:
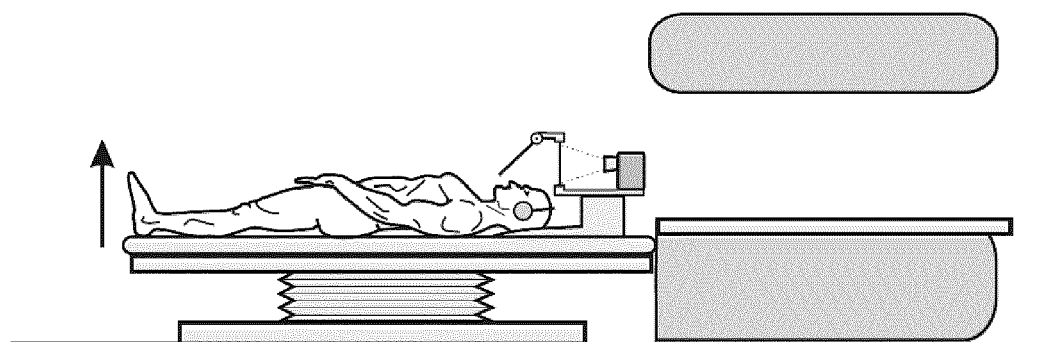
Figure 3C:
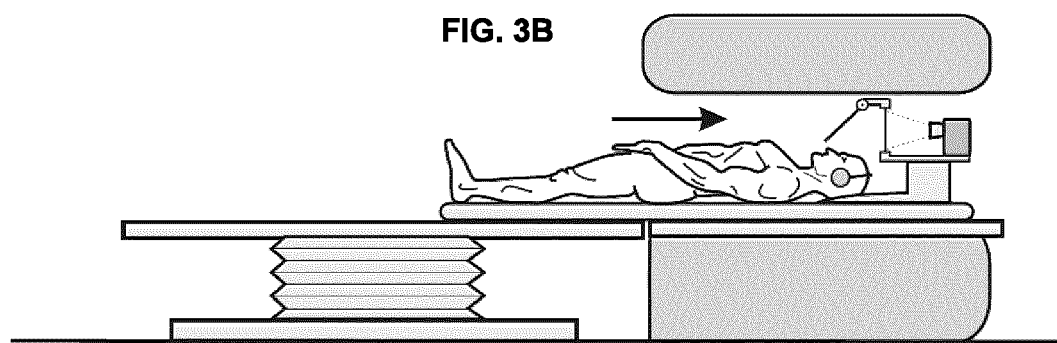

FIGS. 3A-3C illustrate an example embodiment in which the projector 100, the projection screen 110, the viewing mirror 120, and the support frame 105 (the display system) are mounted to the table such that they remain fixed relative to the table as the table is moved in both horizontal and vertical directions. This may be achieved, for example, by attaching the support frame 105 to the top of the table 10. The figures illustrate how the fixed spatial relationship between the projector 100, the projection screen 110, the viewing mirror 120, and the table 10 relative to the table 10 results in projected images that are viewable by the patient during both horizontal and vertical translation of the table 10 such that the projected images maintain a fixed projected field size during translation.

In FIG. 3A, the table 10 is shown in a lowered position relative to the gantry 50, enabling the patient to comfortably lie on the table. The patient lies on the table such that the projection screen 110 is visible to the patient through the viewing mirror 120. The table is then raised to a height suitable for entry into the bore of the gantry 50 while projecting images onto the projection screen 110. Since the projector 100, projection screen 110, and viewing mirror 120 are all supported (by the support frame) relative to the table 10, the separation between both (i) the patient and the projection screen 110 and between (ii) the projection screen 110 and the projector 100, remain constant during vertical translation, and as a result, the projected field remains constant during vertical translation. As a result, the patient images that are presented to the patient do not suffer from translation-dependent artifacts such as changes in focus and/or projected field size. The fixed configuration therefore enables the patient to become immersed in the displayed images during the initial vertical translation of the table 10, reducing the patient's awareness of the vertical translation.

FIG. 3C shows the subsequent horizontal translation of the patient into the bore of the gantry 50. Again, since the projector 100, projection screen 110, and viewing mirror 120 are all supported (by the support frame) relative to the table 10, the separation between both (i) the patient and the projection screen 110 and between (ii) the projection screen 110 and the projector 100, remain constant during horizontal translation of the table, and as a result, the projected field remains constant during horizontal translation. This constancy of the projected field, the filling of the projection screen 110, and the focus of the projected images helps to maintain the immersion of patient in the projected images and assists in reducing the patient's awareness of entering the bore of the gantry 50.

Figure 4:
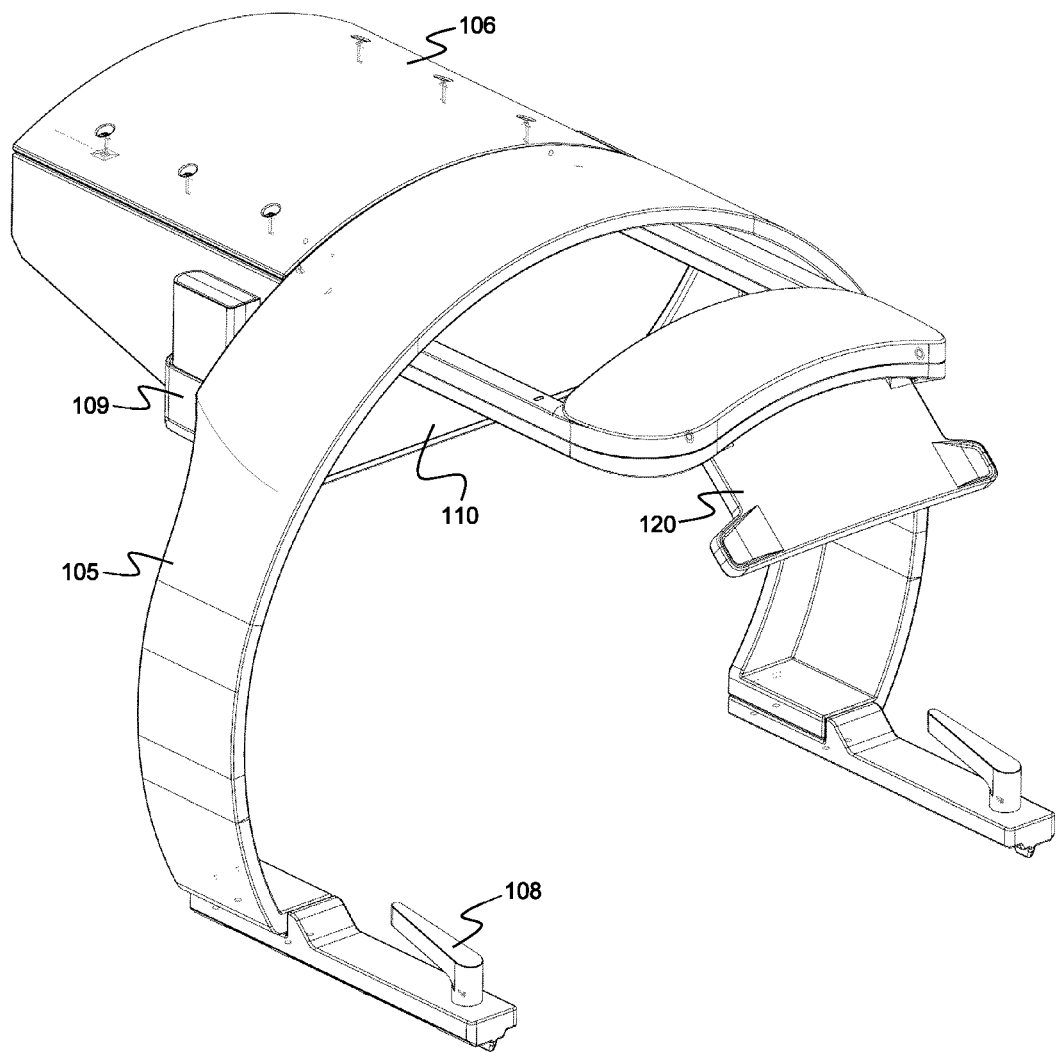
FIG. 4 shows an example implementation of a display system including a projector, a projection screen, and a viewing mirror.

Referring now to FIG. 4, an example implementation of a display system for use with a table of a gantry-based medical imaging or therapeutic system is shown. The display system includes a support frame 105 that mechanically supports a projector, a projection screen 110, and a viewing mirror 120. The projector, and associated projector electronics, are housed within the projector housing 106 that is supported by the support frame 105. As shown in FIG. 4, the projector housing also supports the projection screen 110, thereby enclosing the projector in a volume bounded by the projector housing 106 and the projection screen 110. The viewing mirror 120 may be rotatably or slidably recessed into a support frame of the display system. For example, the viewing mirror may be pivotally mounted to a support frame (e.g. via a hinge), or slidably extendable, such that it may be extended into position during use and recessed when not in use. The viewing mirror may be movable according to a plurality of degrees of freedom, for example, one or more translation degrees of freedom, and/or one or more rotational degrees of freedom. The translation and/or rotation mechanism may include a stop to limit the amount of rotation and/or translation of the mirror.

The support frame 105 is attachable to a table (not shown). In the example implementation shown in the figure, the support frame 105 includes clamps 108 that can engage with rails that reside on the table to secure (e.g. lock) the support frame 105 to the table. It will be understood that the attachment mechanism shown in the figure is but one of many different types of attachment mechanisms that may be employed.

As noted above, the projector housing 106 houses the projector, and may also house electronic components operatively connected to the projector, such as, but not limited to, a power supply, a wireless receiver or transceiver, and antenna. The projector housing may also include a folding mirror that reduces the spatial distance between the projector and the projection screen, while facilitating optical path length between the projector and the projection screen. Also shown in the figure, on the side of the projector housing 106, is a battery dock 109 with a battery inserted that is used to power the projector and the projection electronics.

Figure 5A:
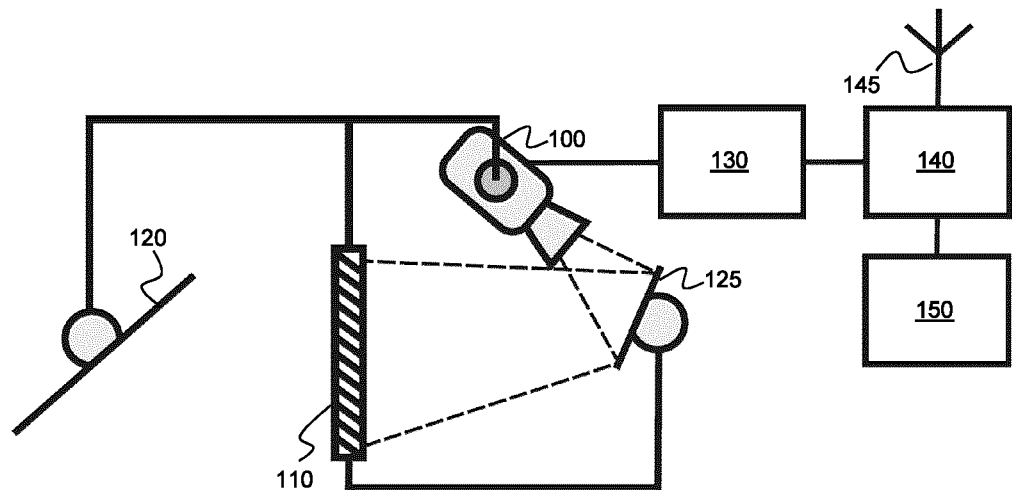
FIGS. 5A, 5B, and 5C show embodiments in which a folding mirror is employed to reduce the size of the display system.

An example of such an embodiment is shown in FIG. 5A, which schematically shows a display system that employs a folding mirror 125 along the optical path between the projector 100 and the projection screen 110. The compact design shown in FIG. 5A enables a reduced size of the projector housing that is well suited for operation within the bore of a gantry such as a magnetic resonance imaging gantry. The example embodiment shown in FIG. 5A also illustrates a wireless display system that is internally powered by a battery 150, and receives media content via a wireless received 140 that is operably connected to an antenna 145. Control circuitry 130 processes the media content received by the antenna 145 and wireless receiver 140 and provides a digital video signal to the projector 100, and delivers suitable power voltages to the projector.

Figure 5B:
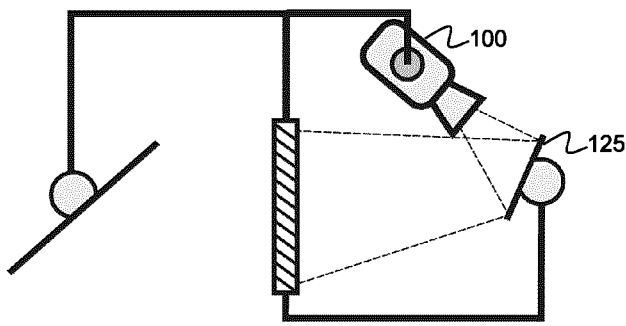
Figure 5C:
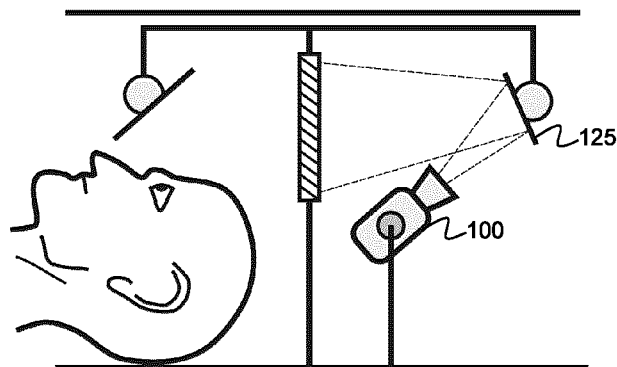

FIGS. 5B and 5C show two example configurations of an embodiment of a folding mirror, showing two different example positions of the projector 100 relative to the folding mirror 125. In FIG. 5B, the projector 100 is located above the folding mirror 125, while in FIG. 5C, the projector 100 is located below the folding mirror 125.

As noted above, in some cases it may be beneficial or important to provide electromagnetic shielding for electrical components of the display system. However, when electronic components are shielded, they may still emit residual emissions within the operational bandwidth of the gantry, such as within the operational bandwidth of a magnetic resonance imaging scanner. In one example embodiment, the effect of these emissions can be further reduced or minimized by positioning the electronics distally from the gantry relative to other components of the display system.

Figure 5D:
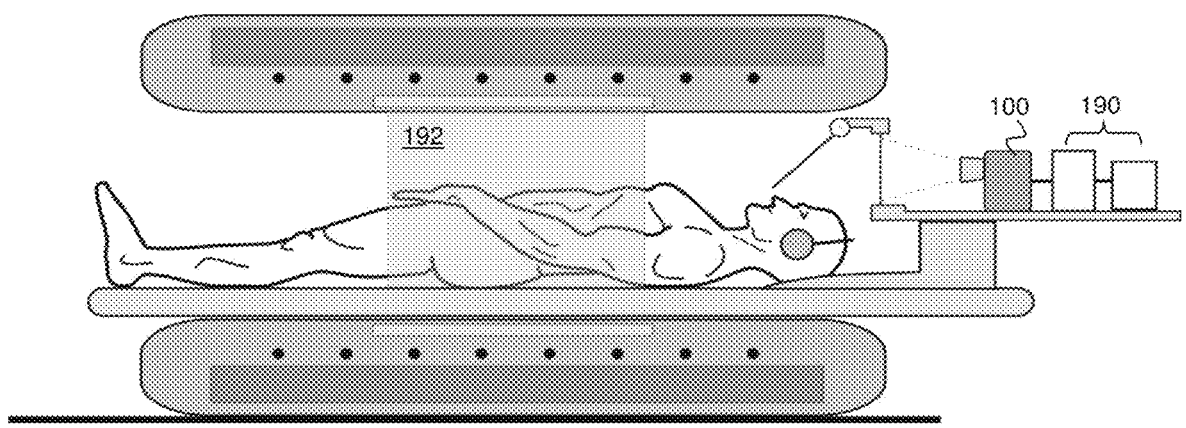
FIGS. 5D, 5E and 5F show embodiments in which electronic components of the display system are positioned distalward, relative to the projector, to reduce the effect of electromagnetic emissions on the operation of the gantry-based imaging or therapeutic device.
Figure 5E:
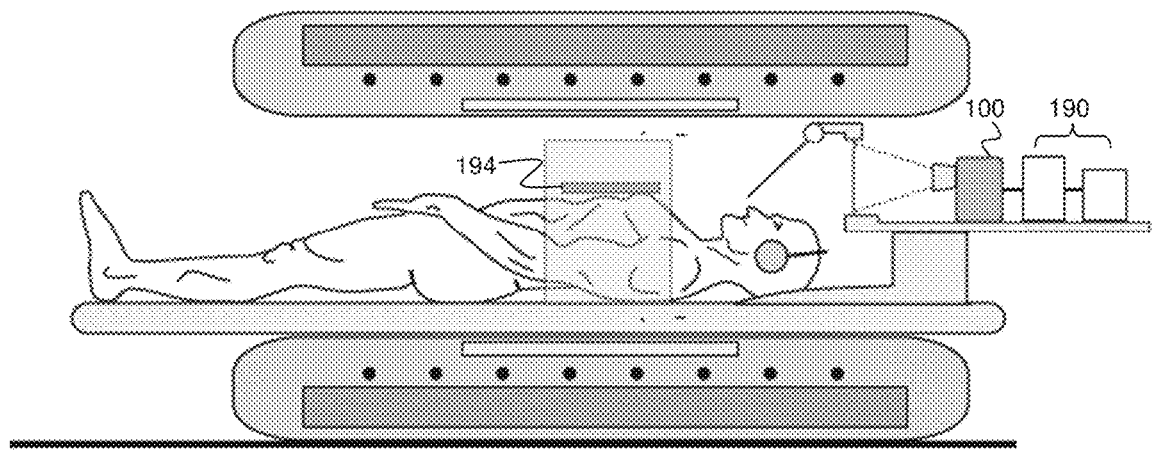
Figure 5F:
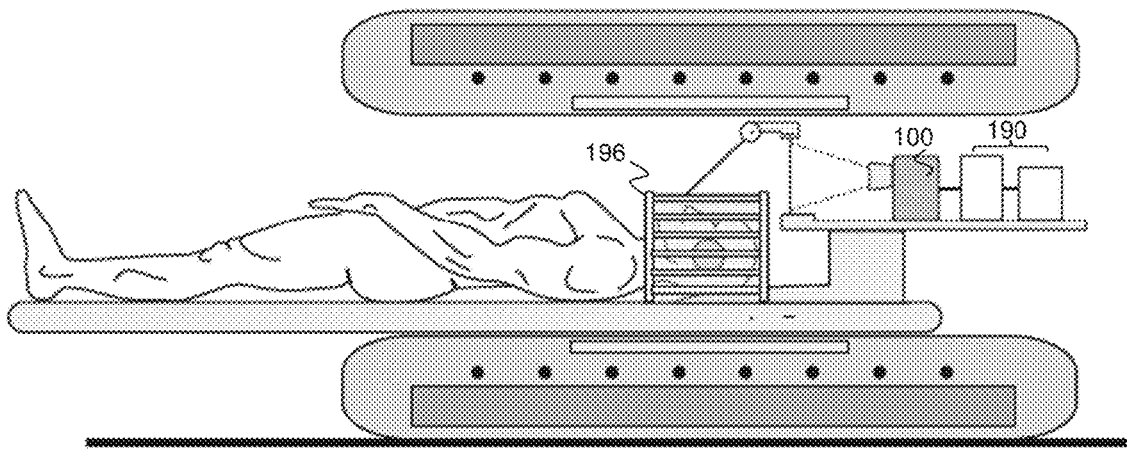

For example, with reference to FIGS. 5D-5F, a magnetic resonance imaging system is shown in which three different receive coil types are employed to perform imaging. In FIG. 5D, a body coil imaging configuration is shown, where the region imaging by the body coil is indicated by 192. In FIG. 5E, a cardiac array coil is shown at 194, while in FIG. 5F, a head coil is shown at 196. The area of sensitivity of each coil is shown as a shaded area. The sensitivity of an imaging coil is highest close to the coils and drops of with distance from the coil. Coils are more sensitive to emissions from devices located within their areas of sensitivity. The further an emitting device is from the region of sensitivity, the less of an effect the emissions will have on the reconstructed images. Accordingly, in each of the example embodiments shown in FIGS. 5D-5F, the electrical components 190 of the display system, such as a power supply, a media processing circuit, and/or a wireless receiver, are located distalward relative to the projector 100 from the components of the gantry that are susceptible to electromagnetic interference (the imaging coils).

Figure 6A:
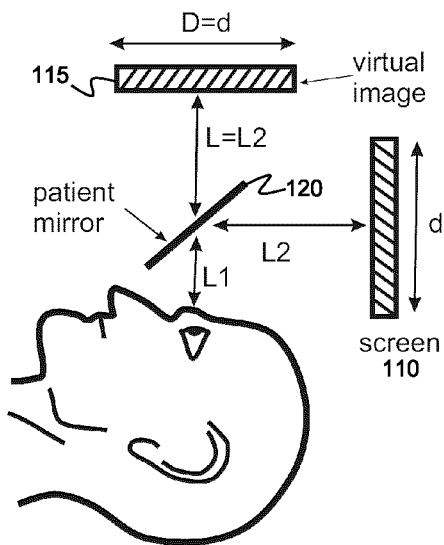
FIGS. 6A, 6B and 6C illustrate example implementations in which a curved viewing mirror is employed to generate a perceived virtual image that resides at a depth that exceeds the optical path length between the patient and the projection screen.

In many example embodiments provided herein, the patient views the images displayed on a projection screen through a viewing mirror. FIG. 6A illustrates an example implementation in which the viewing mirror (also referred to herein as a "patient mirror") is flat. According to such example embodiments, the projected images are perceived by the patient as residing at a depth that is the sum of the optical path length between the patient and the viewing mirror 120, and between the viewing mirror 120 and the projection screen 110. In cases in which the display system is compactly designed, the perceived depth can be small, and may be less than a distance between the patient and an (overhead) inner wall of the gantry 50. In such cases, the short depth of the perceived images may still contribute to a sense of claustrophobia by the patient.

The present inventors have found that the claustrophobic sensation that results from a compact optical design may be circumvented by employing a curved optical element, such as a curved mirror or a lens, to generate a virtual image that is perceived by the patient at a depth that exceeds the optical path length between the patient and the projection screen 110.

Figure 6B:
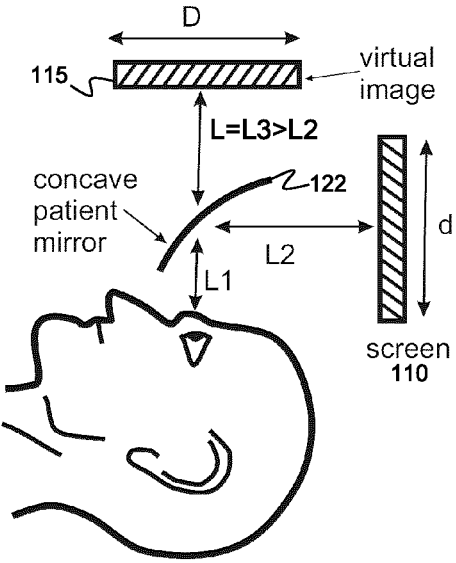

FIG. 6B illustrates an example of such an embodiment, in which the viewing mirror 122 has a concave surface. The reflection of the image of the projection screen 110 by the concave viewing mirror 122 causes the image perceived by the patient to be magnified as a virtual image 115. The virtual image 115 is perceived by the patient to reside at a depth that exceeds the optical path length between the patient and the projection screen 110.

The increased depth of the virtual image can be understood by comparing FIG. 6A to FIG. 6B. In FIG. 6A, the flat mirror viewing mirror 120 is shown at a 45-degree angle with respect to the patient and also with respect to an image projected onto the projection screen 110. The size and distance of the image as seen by the patient is the size of the image at the total path length between the patient's eyes and the projection screen 110, namely L1+L2. However, as shown in FIG. 6B, the concave mirror 122, which is also illustrated at a 45-degree angle with respect to the patient and with respect to the image projected at the projection screen 110, causes the rays to be inwardly directed as they reflect toward the patient. This in turn produces an increase in the size of the perceived virtual image that is seen by the patient. Moreover, the virtual image is perceived at a distance L1+L3 that exceeds the total path length between the patient and the projected image on the projection screen 110.

In some example embodiments, the curvature (e.g. focal length) of the concave mirror is selected such that the virtual image is perceived at a depth that lies beyond a location of an inner surface of the gantry, such as the inner surface of a bore of the gantry. This causes an illusion in which the patient perceives that they are residing in a region that is larger than the true region in which they reside, potentially reducing feelings of claustrophobia and reducing overall patient anxiety. For example, in one example implementation, a concave mirror may be selected such that the perceived size of the gantry bore, perceived as if the images were projected onto the inner surface of the bore, is at least 110%, at least 120%, at least 130%, at least 140%, or at least 150% of the true size of the bore. In one example implementation, the concave mirror is selected to have a focal length such that a 70 cm diameter bore is perceived, on the basis of the projected images, as if it had a diameter of at least 90 cm.

Figure 6C:
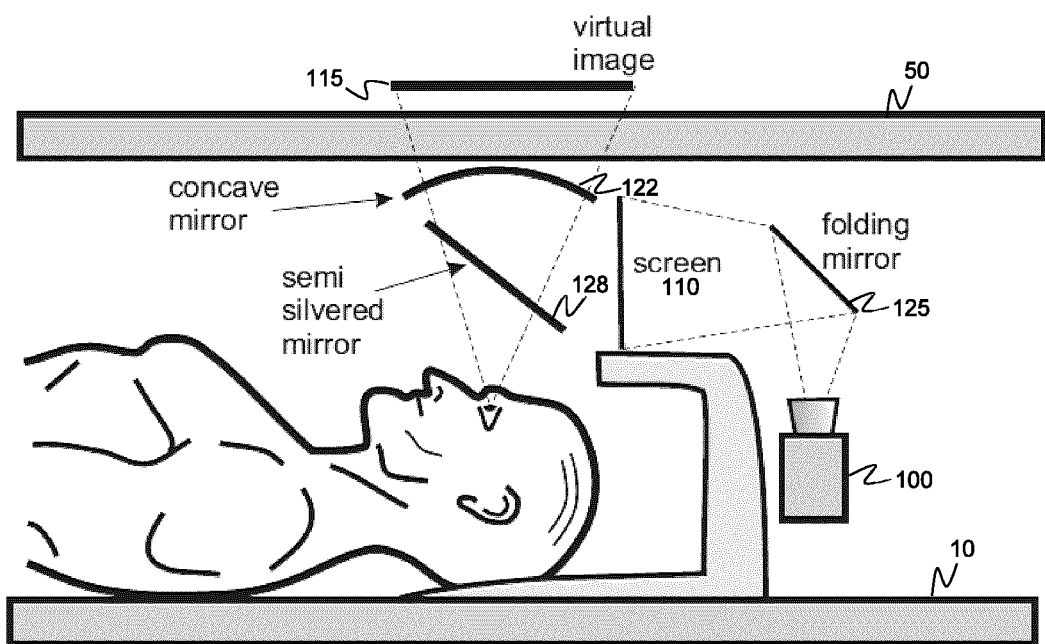

FIG. 6C illustrates another example implementation in which a concave mirror 122 is employed to result in the perception, by the patient, of a virtual image 115 having a depth that lies beyond an inner surface of the gantry 50. However, unlike the example embodiment shown in FIG. 6B, a partially reflective mirror 128 is employed along the optical path between the concave mirror 122 and the projection screen 110, such that the projected light is incident onto the concave mirror 122 along the optical axis of the concave mirror 122. This co-axial configuration causes enables the creation of distortion-free virtual images.

The example embodiment shown in FIG. 6C can be further understood as follows. With reference to FIG. 6C, consider an image projected onto a screen and a concave mirror positioned above the patient where the concave mirror with focal length f is located a distance $L_2$ from the screen and a distance $L_1$ from the patient. The distance of the virtual image of the screen as seen by the patient can be calculated by the thin lens equation:

$$\frac{1}{L_2} - \frac{1}{L_1} = \frac{1}{f},$$

Where $I_i$ is the distance of the virtual image above the concave mirror. This results in a total distance of the virtual image from the patient $L_p$, where:

$$L_p = L_1 + L_i.$$

It should be noted, and understood, by one skilled in the art, that for a virtual image to be formed, a concave mirror can be employed provided that the focal length f is greater than the distance $L_2$ between the curved mirror and the projection screen. The size of the image seen by the patient D at the distance $L_p$ can be calculated to be:

$$D = \frac{l_i}{l_o}d,$$

where d is the size of the image on the screen.

Figure 7:
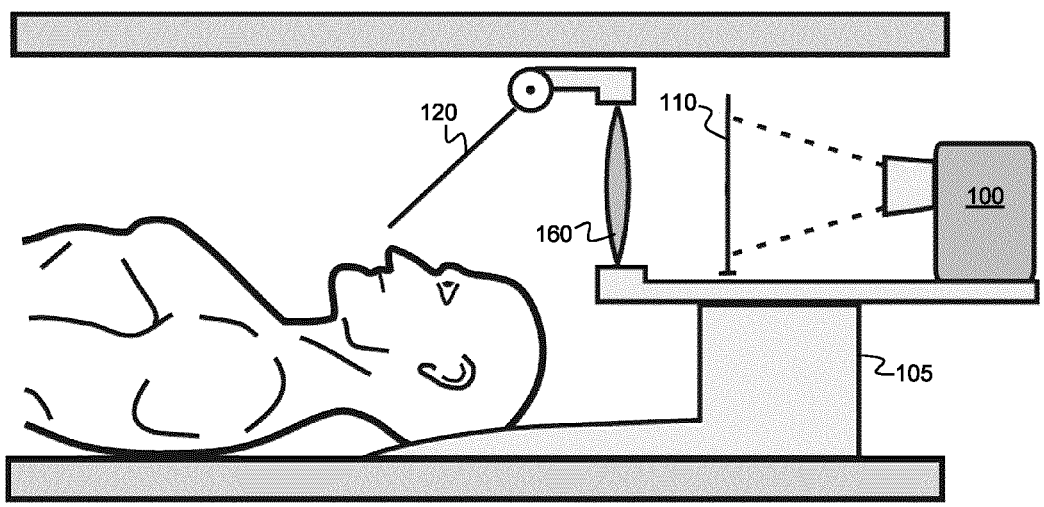
FIG. 7 shows an example embodiment in which a lens is employed to generate a perceived virtual image that resides at a depth that exceeds the optical path length between the patient and the projection screen.

Although the embodiments shown in FIGS. 6B and 6C employ a curved mirror in order to achieve a perceived virtual image depth that exceeds the optical path length, and optionally exceeds the distance from the patient to the inner surface of the gantry, it will be understood that a similar outcome can be achieved using either a lens or a combination of a lens and a mirror. FIG. 7 illustrates an example implementation in which the viewing mirror 120 is a flat mirror, and a lens is provided between the projection screen 110 and the viewing mirror 120. In another example implementation, the viewing mirror 120 may also be curved, such that the combination of the curved viewing mirror 120 and the lens produces the desired increase in perceived image depth. It is also noted that the example embodiment illustrated in FIG. 6C may also be adapted to include an intermediate lens between the partially reflective mirror 128 and the projection screen 110. It will be understood that the single lens shown in FIG. 7 is merely for illustrative purposes, and that one or more lenses may be employed in order to produce the desired virtual image offset.

Referring to the mathematical description of the curved mirror example embodiments that is provided above, it will be understood that the same equations may apply to example embodiments involving a lens, where $L_2$ is the distance between the lens and the screen and $L_i$ is the distance of the virtual image formed beyond the lens and f is the focal length of the lens. Again, it should be noted, and understood, by one skilled in the art, that for a virtual image to be formed, a converging lens should be employed if the focal length f is greater than the distance Io between the lens and the screen.

In order to limit the weight and thickness of lenses (which tend to be large aperture and relatively short focal length) one or more Fresnel lenses may be employed. Fresnel lenses can take to form of flat sheets to enable easy mechanical integration and are also typically made of durable plastic materials.

Figure 8:
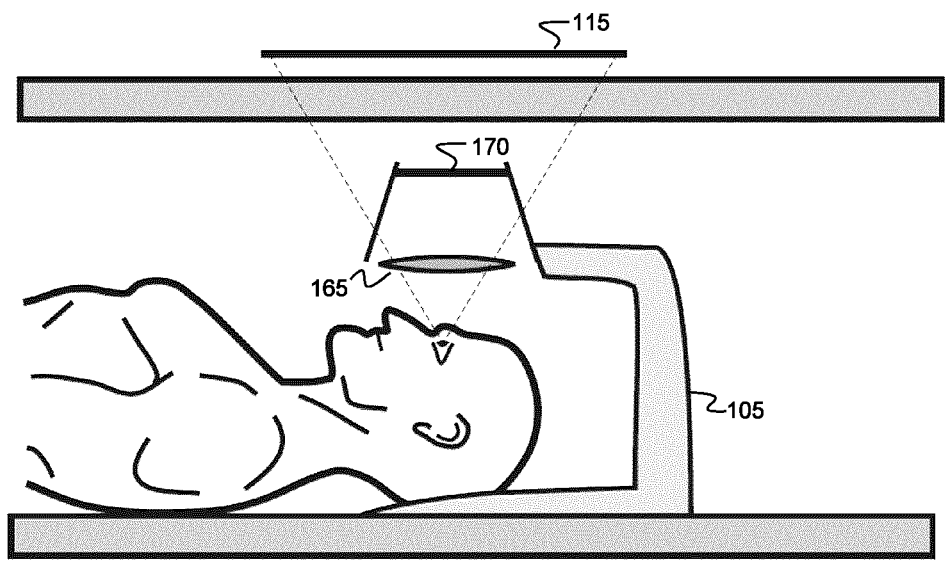
FIG. 8 shows an example in which a lens is employed to generate a perceived virtual image of a flat panel display, where the virtual image is perceived to reside at a depth the exceeds the depth of the flat panel display.

FIG. 8 illustrates another example embodiment in which a flat panel display 170 is supported overhead the patient using a support frame 105. In applications in which the gantry is a magnetic resonance imaging gantry, the flat panel display is a magnetic resonance imaging compatible display. For example, a shielded LCD screen can be used where the front (visible) face of the screen is shielded with a metallic porous mesh. Alternatively, flat panel screens can be used that have been made to be free of radio-frequency emissions that lay within the operations bandwidth of the MRI. Furthermore, the flat panel screen should be generally free of ferromagnetic materials such as stainless steel which may be use as support structures in the panel. In other applications in which the gantry is not a magnetic resonance imaging gantry, the flat panel display need not be magnetic resonance imaging compatible.

In other example embodiments involving a flat panel display, any one of the preceding example embodiments that employ a combination of a projection screen and a projector may be adapted such that the combination of the projection screen and the projector are replaced by a flat panel display. As noted above, in applications in which the gantry is a magnetic resonance imaging gantry, the flat panel display is a magnetic resonance imaging compatible display. However, in other applications in which the gantry is not a magnetic resonance imaging gantry, the flat panel display need not be magnetic resonance imaging compatible.

Figure 9A:
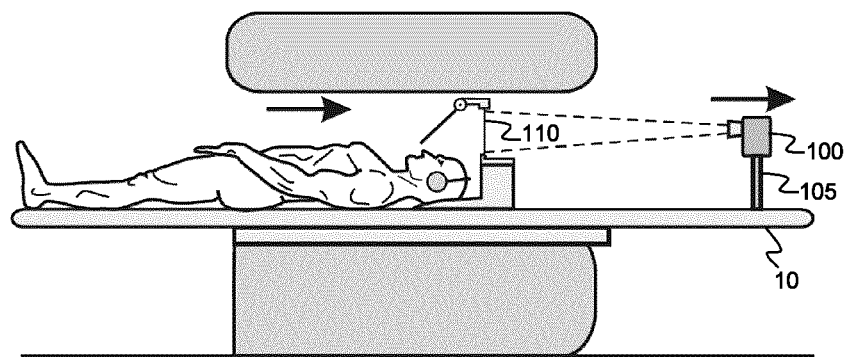
FIGS. 9A, 9B, 9C, 9D, and 9E show various example embodiments in which an external movable projector is employed to maintain a constant project field size as the table is moved horizontally relative to the gantry.
Figure 9B:
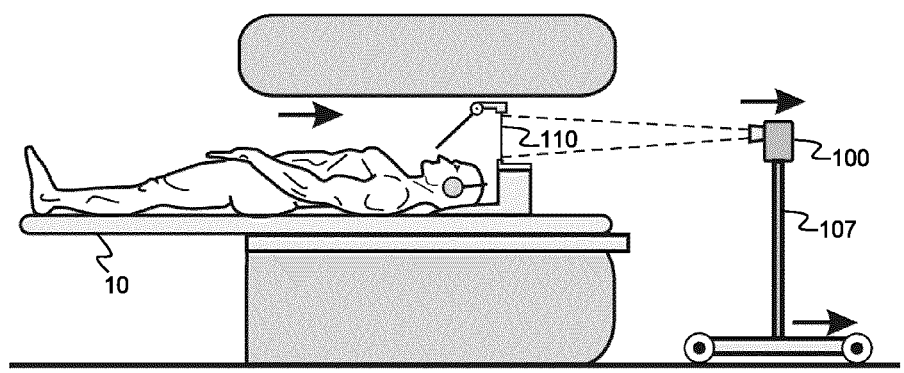
Figure 9C:
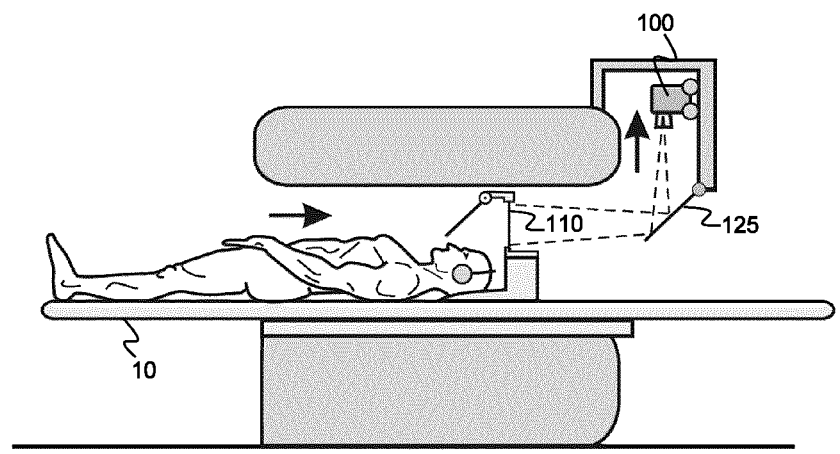

Referring now to FIGS. 9A-9C, additional example embodiments are disclosed that preserve the position of the projector relative to the projection screen during translation of the table. In FIG. 9A, an example embodiment is provided in which the position of the projector 100 is fixed relative to the table by a support frame 105 such that the projector 100 remains outside of the bore of the gantry 50 as the patient is translated to different locations within the bore. In the case of a magnetic resonance imaging gantry, the present example embodiment may permit the use of a projector (and associated electronics) that is not compatible with use within the gantry bore.

FIG. 9B shows an alternative example embodiment in which the projector 100 is not mechanically attached to the table 10, but where the projector 100 is translatable. In the example implementation shown in the figure, the projector 100 is supported by a movable frame 107. The movable frame may be translated in unison with the table as the table is moved relative to the gantry in order to maintain a constant spatial offset between the projector 100 and the projection screen 110. This translation of the projector 100 may be manual, or automated. For example, the movable frame 107 may be motorized and operably connected to the control and processing system, such that the translation of the projector 100 by the movable frame 107 can be controlled to be synchronous with the translation of the table 10. One or more position sensors may be employed to control the position of the projector in a closed-loop manner. It will be understood that the example embodiment shown in the figure is but one example implementation of a movable projector, and that many other configurations may be employed to permit and optionally control external translation of the projector 100, such as rail-based systems where the projector is translatable on one or more linear rails. It will be understood that the example embodiment shown in FIG. 9B permits the movable projector 100 to reside in the same room as the gantry, or in an adjoining room (where the project delivers the projected images through a window).

FIG. 9C presents an alternative example embodiment in which the projector 100 resides outside of the bore of the gantry, and where the folding mirror 125 is employed to recess the projector in an external angled configuration relative to the horizontal direction. In the example implementation shown in the figure, the folding mirror 125 is angled at 45 degrees, but other angular configurations may be employed without departing from the intended scope of the present example embodiment. According to the present example embodiment, the projector 100 movable along a linear rail supported relative to the gantry in order to preserve the spatial offset between the projector 100 and the projection screen 110. The projector is movable along the linear rail using a motor or other linear actuator that controlled by the control and processing system.

Figure 9D:
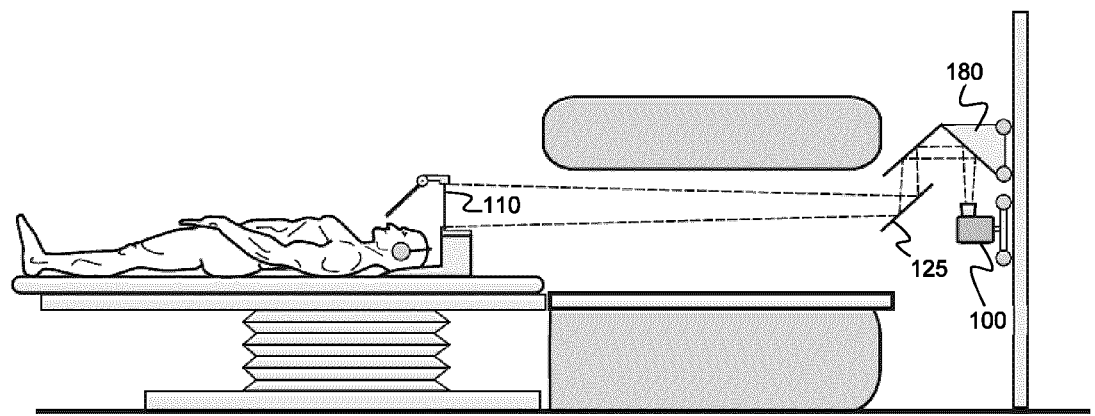
Figure 9E:
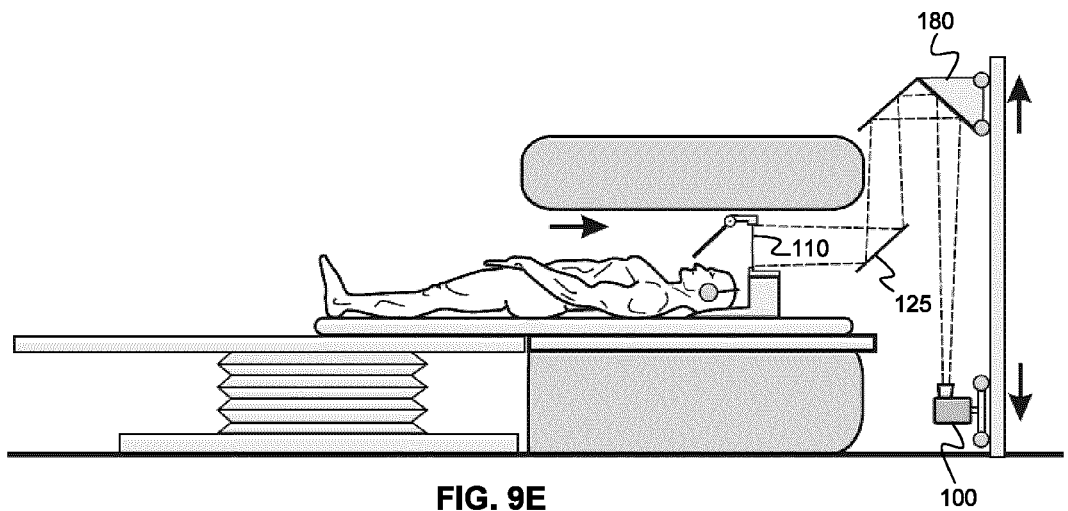

FIGS. 9D and 9E illustrate an alternative example embodiment that accommodates a larger range of table motion in comparison to the example embodiment shown in FIG. 9C. In the example embodiment shown in FIG. 9C, the position of the projector 100 is controlled such that when the horizontal position of the table is varied, the vertical position of the projector is correspondingly varied in order to maintain a fixed optical path length between the projector 100 and the projection screen 110. However, the range of horizontal table travel that can be accommodated by vertical projector travel is limited to the vertical travel span of the projector 100. The example embodiment in FIGS. 9D and 9E achieves an increased range of accommodated table motion by including a retroreflector 180 that achieves additional folding of the optical path. Moreover, in some example embodiments, such as the example embodiment shown in FIGS. 9D and 9E, the both the retroreflector 180 and the projector 100 are controllably positionable in the vertical direction. By controlling the vertical positioning of both the retroreflector 180 and the projector 100, the difference between the maximum and minimum lengths of the portion of the optical path residing between the folding mirror 125 and the projector 100 can be further increased, thereby increasing the corresponding range of horizontal motion of the table that can be accommodated.

Figure 10A:
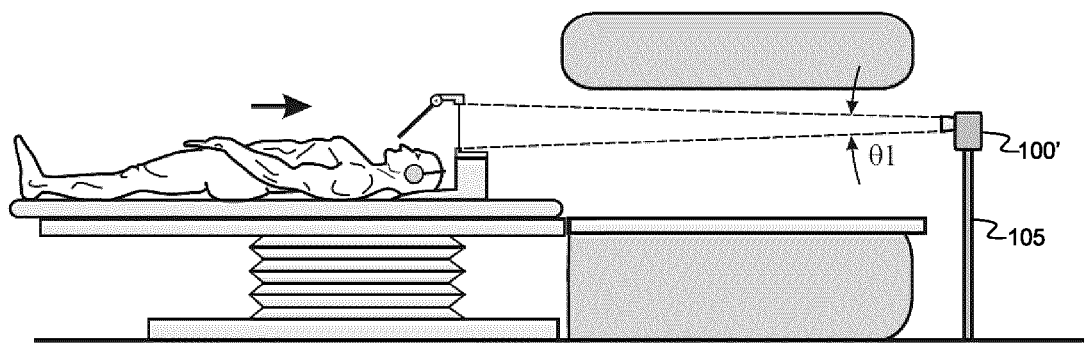
FIGS. 10A and 10B show example embodiments in which a variable throw projector is employed to maintain a constant projected field size on the projection screen.
Figure 10B:
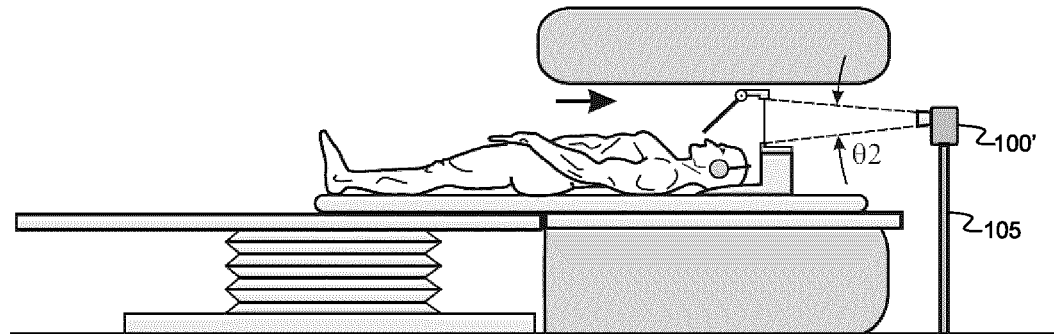

Referring now to FIGS. 10A and 10B, an alternative example embodiment is shown in which an external projector 100' is employed to project images onto a projection screen 110, where the projection screen 100 is fixed relative to the table. As in the previous example embodiments, the projection screen 110 is supported relative to the table such that the projection screen 110 moves in a common reference frame with the table and the patient during translation of the table. However, unlike the preceding example embodiments, the position of the projector is not fixed relative to the table in the present embodiment. Therefore, the projector 100' and the projection screen 110 no longer reside within a common reference frame, and only the projection screen 110 resides in a co-moving reference frame with the patient.

If a fixed throw/focus projector is used in such a configuration, the lack of common reference frame for the projector and the projection screen 110 would result in position-dependent changes in the projected field size (the size of the field that is projected onto the projection screen). This problem is overcome in the example embodiment shown in FIGS. 10A and 10B by employing a projector that incorporates or is optically interfaced with a controllable optical assembly that permits control of the throw of the projector 100', such that the projected field size of the projector is maintained at different throw values of the projector. The projector 100' is operably connected to the control and processing system such that the projected field of the projector 100' is varied as the table is moved, such that the projected field size on the projection screen 110 is maintained. This can be achieved, for example, using a variable throw projector. A variable throw projector can be achieved through the use of a zoom lens assembly that re-arranges the lenses inside the assembly to produce a larger or smaller image without moving the projector. A motorized zoom facility can be controlled to vary the lens configuration automatically. Several off-the-shelf zoom lenses for projectors are available.

In another example implementation, this functionality can be achieved by cropping the image (digital zoom), where the amount of digital cropping is dependent on the position of the table, and where the amount of digital cropping is selected, as a function of table position, such that the size of the field that is projected onto the projector screen is independent of table position.

As noted above, many of the example embodiments of the present disclosure may be beneficial in reducing patient anxiety during medical imaging and/or therapeutic procedures in which the patient is translated, on a table, relative to a gantry. This reduction in anxiety may be achieved, for example, through a more immersive patient viewing experience that occurs when the images are projected to the patient while preserving the projected field size during table motion. Furthermore, in some example embodiments described above, a reduction in patient anxiety may be achieved by projecting images as virtual images that are perceived by the patient as residing at a depth that extends beyond the confined spatial region in which the patient resides.

In an additional example embodiment, patient anxiety may also be reduced by delivering images and/or video with content (as opposed to a projected field size) that changes as the patient is translated closer to the gantry (e.g. translated into the bore of a gantry, and/or translated to a position at which imaging and/or treatment is to be performed). Such changes in image content may be selected such that as the patient moves relative to the gantry, the images convey a sense of moving from into an environment that promotes an increased sense of relaxation. The changing image content may also be synchronized with a change in audio that is delivered to the patient, optionally in addition to other sensory changes, such as the introduction of scents that are intended to promote relaxation. For example, the images may be selected such that the patient senses that they are transitioning into a scenic setting such as a beach or waterfall, or to a relaxing setting such as a spa setting.

In one example implementation, the perception of a transition as the table is moved relative to the gantry can be achieved by playing a recorded video of a transition into a scenic setting, where the playback speed is controlled to match the velocity of the table as measured by a table position sensor or a table mounted accelerometer. In one example implementation, the video playback can be started when the table motion sensor detects table movement and the video playback can be stopped when the sensor detects that table movement has stopped.

Alternatively, a series of still images can be stored that comprise a transition video in memory where each image corresponds to a specific table position. The image corresponding a specific table location can be displayed to the patient when the table is detected to be in that position by a table location sensor or as calculate by a table-mounted accelerometer. The images can be updated at a frame rate such that they appear to the patient to be part of a continuous video.

In another example embodiment, the content of the displayed images could be altered in such a manner to match the sensation of vertical motion of the couch during vertical translation. An example, would include an image of clouds that would appear to become slightly closer as the patient is raised into the position for insertion into the bore of the gantry. By this means, the sense of immersion the patient would experience would be enhanced as it matches the physical sensation of vertical motion the patient would experience during this phase of the couch positioning.

In some example embodiments, a motion tracking and correction subsystem for the tracking and correction of patient motion may be integrated with a display system in order to support the simultaneous tracking and correction of patient motion with the presentation of images to a patient during a medical procedure.

A non-limiting example of a such a motion tracking and correction subsystem is one that consists of optical cameras that are fixed to the top surface of an MRI scanner bore (above the patient). During use, the patient wears a fiducial marker, the position of which is tracked by the cameras. Motion correction techniques may then be employed (e.g. during an MRI pulse sequence) to correct for the detected patient motion. Duyn et al. (WO 2009/129457) discloses an example of such a motion tracking subsystem where cameras can be used to correct for motion by receiving a plurality of images from a scan of a subject with a camera, receiving magnetic resonance imaging (MRI) images obtained concurrently with the scan, correlating the plurality of images obtained from the scan with the MRI images, resulting in motion correction data, and providing the motion correction data to an MRI system, wherein the MRI system adjusts scanning according to the motion correction data.

It will be understood that the motion correction subsystem described above represents a non-limiting example of a motion tracking and correction subsystem. However, the example embodiments disclosed herebelow may employ a wide variety of motion tracking and correction subsystems (which may use, for example, passive or active fiducial markers for motion detection) for use with a wide variety of medical diagnostic and/or treatment systems.

Figure 11A:
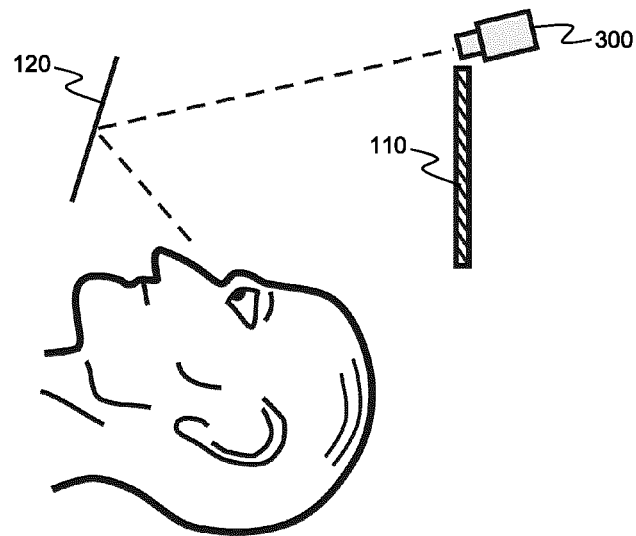

Referring now to FIG. 11A, an example embodiment is illustrated in which at least one motion tracking camera 300 of a motion tracking and correction subsystem is integrated with a display system. The display system includes a projector (not shown), a projection screen 110 onto which images are projected, and a viewing mirror 120. As shown in the figure, the mirror 120 is employed by the beam paths of both the viewing of the projection screen 110 and the detection of a fiducial (or patient anatomy) by the motion tracking camera 300. Accordingly, in some example embodiments, at least one optical component is shared by both the motion tracking of both the motion tracking subsystem and the display subsystem.

In some example implementations, the motion tracking camera 300 may be mechanically supported with one or more components of the display system by a common support frame. For example, one or more motion tracking cameras 300 may be mechanically supported by a support frame that also supports one or more of the projector, the projection screen 110, and the mirror 120. In some example embodiments, the mirror 120 may be supported by a head coil, and one or more motion tracking cameras 300 may be supported by a support frame that also supports the projection screen 110.

Figure 11B:
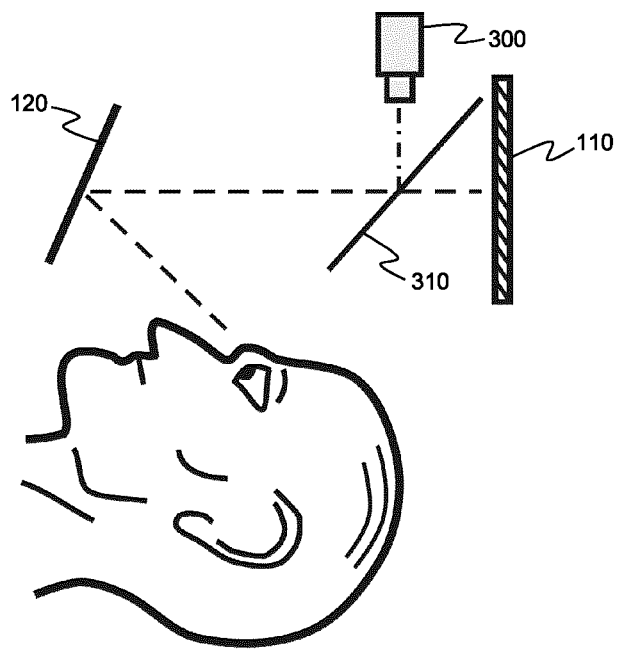

FIG. 11B illustrates an alternative example embodiment in which a partially reflective mirror 310 is positioned at an oblique angle between the mirror 120 and the projection screen 110. The additional mirror is positioned such that the beam path between the motion tracking camera 300 and a fiducial (not shown) on the patient includes reflection from the partially reflective mirror 310, while the viewing of the projection screen 110 by the patient involves transmission through the partially reflective mirror 310. In an alternative example implementation, the partially reflective mirror may be replaced with a spectrally reflective mirror that is configured to reflect optical energy that is within a pre-selected operational bandwidth of the motion tracking and correction subsystem.

Figure 11C:
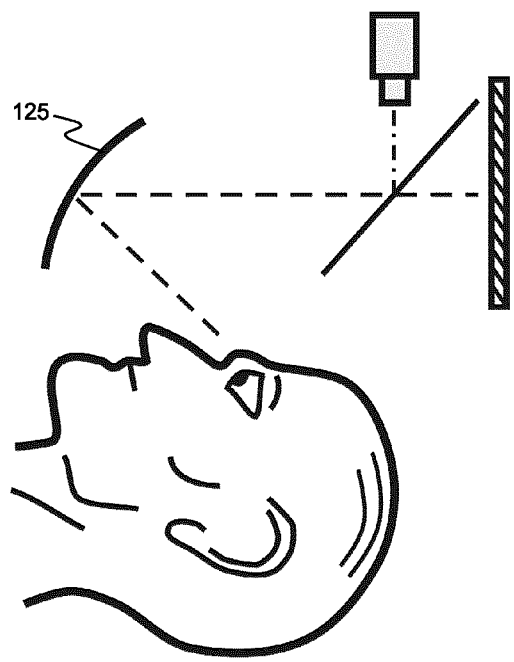
Figure 11D:
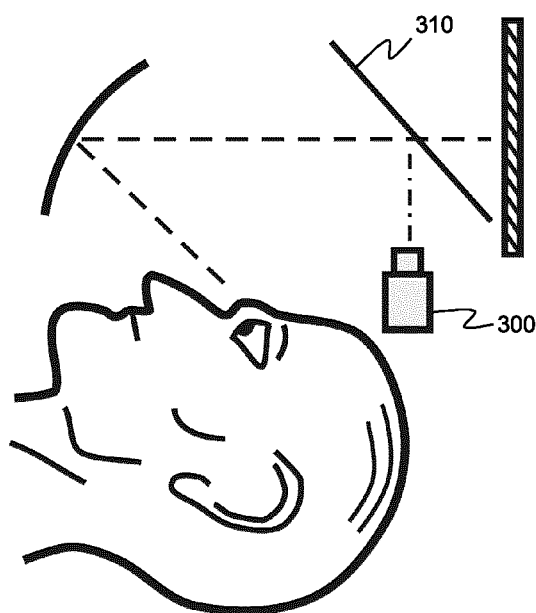

FIGS. 11C and 11D illustrate additional example implementation which the mirror 125 is curved and the motion tracking camera 300 is located proximal to the patient (i.e. closer to the patient than the upper inner surface of the gantry, relative to the additional mirror 310), respectively.

Figure 11E:
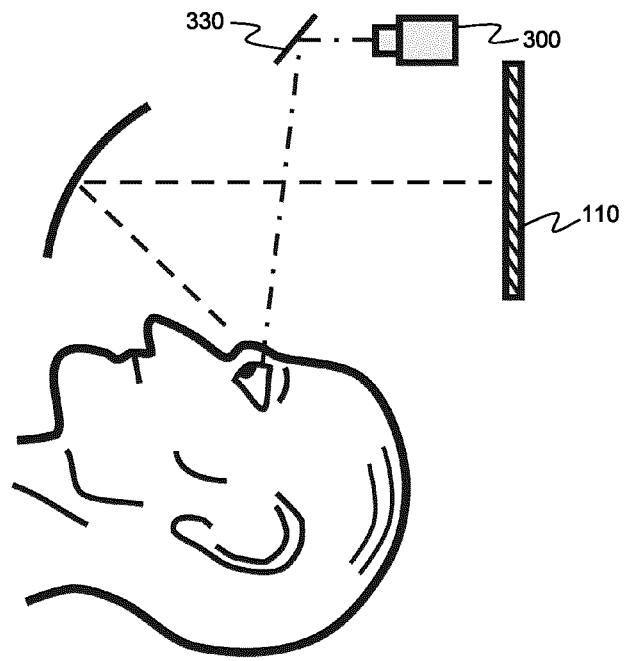
Figure 11F:
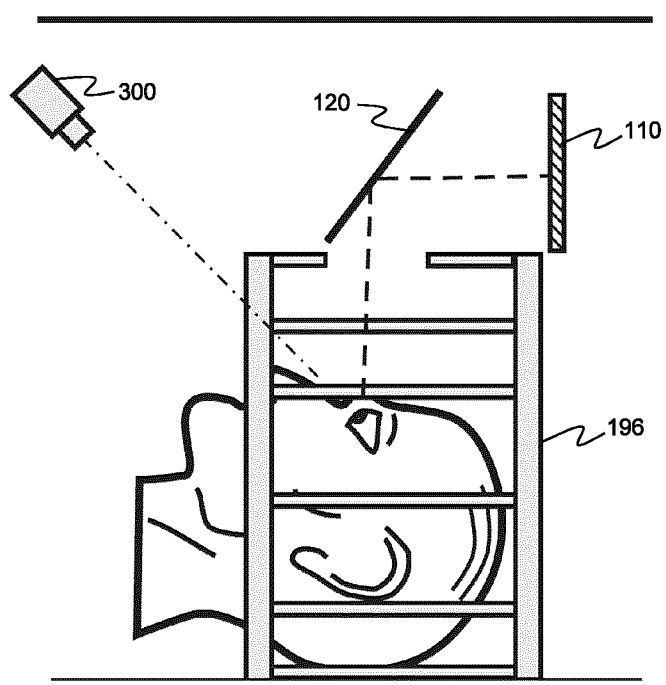
Figure 11G:
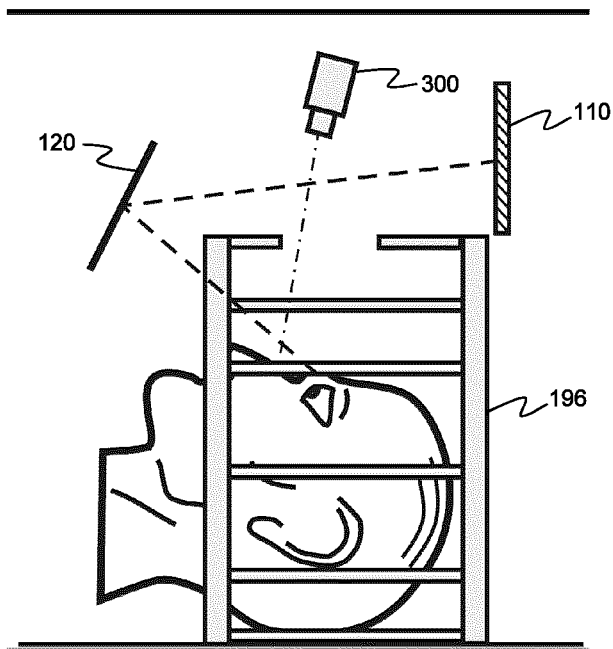

FIG. 11E illustrates an example embodiment in which an additional mirror 330 is employed to reflect light detected by the motion tracking camera 330. This additional mirror does not reside along the optical path employed by the patient to observe the projection screen 110. Accordingly, the motion tracking camera is positioned such that a beam path associated with detection of a fiducial worn by the patient (or detection of patient anatomy) is unimpeded by the mirror 120 and the projection screen 110. FIGS. 11F and 11G also show example embodiments in which the motion tracking camera 300 is positioned such that a beam path associated with detection of a fiducial worn by the patient (or detection of patient anatomy) is unimpeded by the mirror 120 and the projection screen 110.

Figure 11H:
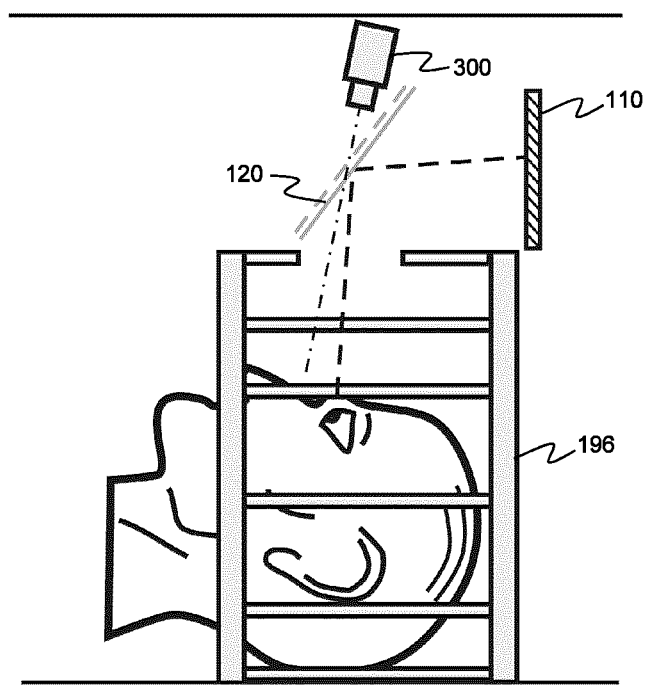

Another example embodiment is illustrated in FIG. 11H, in which the mirror 120 is either a partially reflective mirror or a spectrally selective mirror, such that the mirror 120 is employed as a transmissive optical component for the motion tracking camera 300 and a reflective optical component for the display subsystem. As shown in FIG. 11H, the optical beam path associated with motion tracking need not be aligned (parallel or coincident) with the optical beam path associated with viewing of the projection screen 110.

Figure 11I:
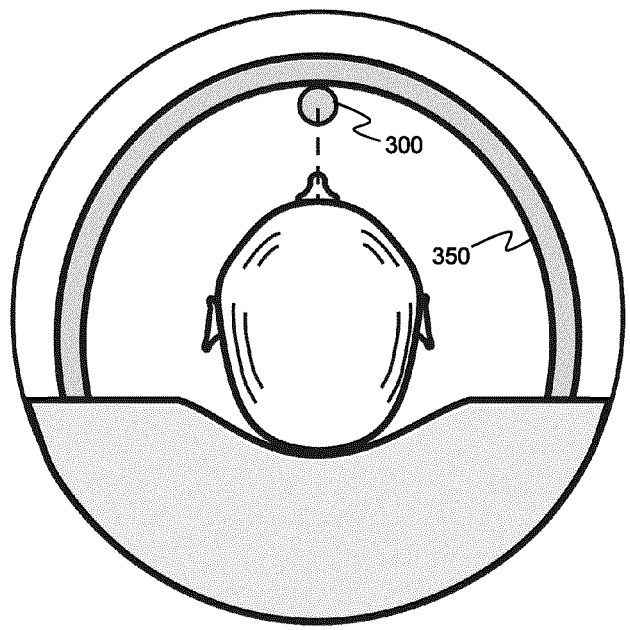
Figure 11J:
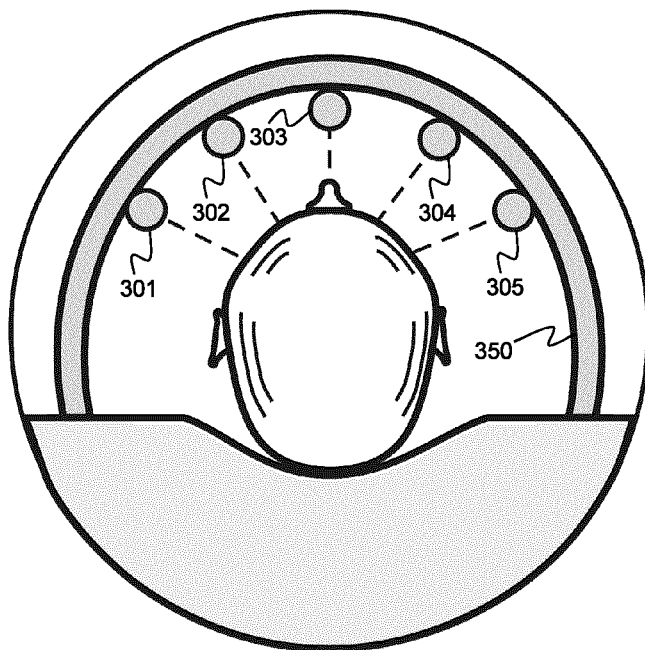

In the embodiments described above, it will be understood that one or more motion tracking cameras 300 may be supported by a support frame that also supports one or more components of the display subsystem or may be supported separately. For example, one or more motion tracking cameras may be supported (e.g. attached to) the gantry, where sufficient clearance is provided beneath the motion tracking cameras to permit relative translation of the display system without mechanical interference. FIGS. 11I and 11J show example embodiments in which one motion detection camera 300 (FIG. 11I) or a plurality of motion detection cameras 301-305 (FIG. 11J) are supported by a support frame 350 associated with one or more components of the display system.

While the example embodiments shown in FIGS. 11A-11J employ the projection of images onto a projection screen 110, it will be understood that other display devices and modalities may be employed in the alternative, such as the use of a flat panel display (e.g. a magnetic resonance imaging compatible display). Although many of the preceding example embodiments have been disclosed within the example context of a magnetic resonance imaging system having a movable table and a gantry, it will be understood that the example embodiments described herein may be adapted to other types of gantry/table based imaging systems and to gantry/table based therapeutic systems (and optionally medical systems that employ both imaging and therapeutic devices supported by a gantry). For example, the example embodiments disclosed herein may be employed with other gantry-based medical imaging systems such as, but not limited to, computed tomography imaging and positron emission tomography imaging. The example embodiments disclosed herein may also be applied to gantry-based therapeutic systems such as radiation treatment systems and robotic surgical systems.

Figure 12:
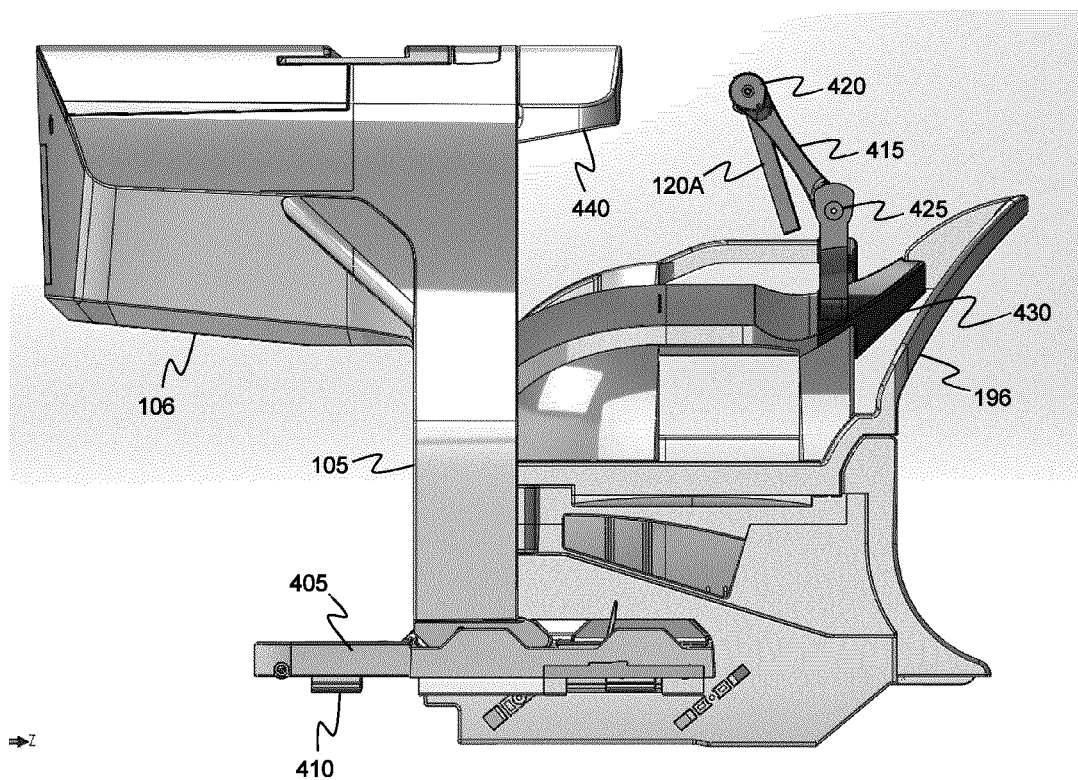
FIG. 12 shows an example implementation of a display system that employs a head coil to support an optional secondary mirror.

FIG. 12 illustrates an example embodiment of a display system in which a viewing mirror 120A is attached to a head coil 196. The example display system, which is similar to that shown in FIG. 4, includes a projector housing 106 which houses the projector and supports the projection screen. The projector housing 106 is supported by a pair of support members 105. Each example support member 105 is removably attachable to a rail system of a table via a corresponding mounting member 405. The mounting member 405 is insertable into the rail of the table and a locking mechanism, such as locking tab 410, creates a cramming action to grip the rail, thereby holding the mounting member 405 to the table (bed). The support member 105 may then be clamped onto the mounting member 405. The present example embodiment permits the mounting member 405 to be rigidly attached to the table.

As can be seen in the figure, the viewing mirror 120A is connected to the head coil 196 (e.g. the upper portion of a head coil) through an example connection assembly that includes an extension member 415 and a pair of pivot joints 420 and 425. The viewing mirror 120A may be rotatably or slidably positioned relative to the head coil 196. For example, the viewing mirror 120A may be pivotally mounted to the head coil (e.g. via a hinge), or slidably extendable. While FIG. 12 illustrates an example embodiment that provides two rotational degrees of freedom, the viewing mirror 120A may, in other example embodiments, be movable according to a plurality of degrees of freedom, for example, one or more translation degrees of freedom, and/or one or more rotational degrees of freedom. The translation and/or rotation mechanism may include a stop to limit the amount of rotation and/or translation of the mirror 120A.

The example connection assembly shown in FIG. 12 includes a base 430 that is connectable (e.g. via a fastener or clamp) to the head coil 196. The top half of the head coil is shaped similar to a mask and is designed so that it can be installed after the patient's head is laid onto the bottom half. The top half (mask portion) typically has large perforations (apertures or windows) to enable the patient to see and breathe therethrough. The members (e.g. rails, beams or bars) that form the boundaries of these perforations are suitable for interfacing with the mirror holder (e.g. via a clamp or a friction fit). For example, by matching the base to the shape of multiple rails, the mirror holder base may be snap-fit onto the mask and remain fixed in space.

In some example implementations, the viewing mirror 120A may be the only viewing mirror of the display system. However, in other example embodiments, the viewing mirror 120A may be a secondary (e.g. optional) viewing mirror that may be optionally installed to the head coil when a primary viewing mirror (shown in FIG. 4) is not employed. For example, referring to FIGS. 4 and 12, the primary viewing mirror 120 shown in FIG. 4 may be recessed or otherwise stowed (e.g. stored within region 440 of FIG. 12, or removed), and the secondary mirror 120A for FIG. 12 may be used in the alternative. The latter configuration, in which the primary mirror 120 is not used but the secondary mirror 120A is employed, may be beneficial in cases involving the use of a motion tracking system by providing an open region between the projector housing 106 and the secondary mirror 1208 that permits the unobstructed use of the tracking system to track motion of the patient's head.

The phrase "gantry", as used herein, is intended to refer to any mechanical support system that is employed to support a medical imaging and/or medical therapeutic device relative to a movable table. Although the preceding example illustrate a closed gantry in the form of a magnetic resonance imaging gantry having a central bore in which a patient can be translated on a table such that the patient is azimuthally surrounded by the gantry, it will be understood that the gantry need not completely surround the patient. For example, a magnetic resonance imaging gantry may be a so-called "open bore" gantry that does not completely surround the patient. In the example embodiments listed above that do not involve magnetic resonance imaging, the gantry may be, for example, a C-arm or an O-arm. In other example embodiments, such as examples involving robotic surgical procedures, the gantry may be mechanical linkage that is controllable to position a medical device or instrument relative to a patient that is positionable on a table.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A magnetic resonance imaging system comprising:
   a magnetic resonance imaging gantry having an inner bore;
   a table translatable relative to the magnetic resonance imaging gantry;
   a projector;
   a projection screen, wherein the projection screen is positioned, relative to the projector, to provide a display surface for images projected by the projector; and
   a mirror supported relative to the projection screen such that the images projected onto the projection screen are viewable through the mirror by a patient when the patient is residing on the table;
   wherein the projector, the mirror and the projection screen are supported relative to the table such that they move in unison with the table while maintaining a fixed spatial relationship therebetween, and such that images projected by the projector onto the projection screen during translation of the table are projected with a constant projected image field size, thereby reducing a perception of motion by the patient as the patient is translated relative to the magnetic resonance imaging gantry
   wherein the mirror, the projector and the projection screen are positionable within the bore of the magnetic resonance imaging gantry such that (i) the mirror resides within a body coil imaging region of the magnetic resonance imaging gantry and (ii) the projector resides outside the body coil imaging region without extending beyond an end of the magnetic resonance imaging gantry.

2. The system according to claim 1 wherein the mirror is a first mirror, and wherein the system further comprises a folding mirror supported such that images projected by the projector are reflected by the folding mirror prior to being projected onto the projection screen.

3. The system according to claim 1 wherein the mirror is a concave mirror, and wherein a focal length of the concave mirror is greater than a distance between the concave mirror and the projection screen, such a magnified virtual image of the projection screen is perceived by the patient.

4. The system according to claim 3 wherein the concave mirror is configured such that the magnified virtual image is perceived by the patient at a depth that extends beyond an overhead inner surface of the magnetic resonance imaging gantry.

5. The system according to claim 1 further comprising a lens supported between the mirror and the projection screen, such that a magnified virtual image of the projection screen is perceived by the patient.

6. The system according to claim 5 wherein the lens is configured such that the magnified virtual image is perceived by the patient at a depth that extends beyond an overhead inner surface of the magnetic resonance imaging gantry.

7. The system according to claim 1 wherein the projector, the projection screen and the mirror are supported by one or more support frames, wherein each support frame is secured to the table such that each support frame moves in unison with the table when the table is translated.

8. The system according to claim 7 further comprising a head coil secured to the table, wherein the mirror, the projector, and the projection screen are secured relative to the table such that when the table is positioned with the head coil in the middle of the longitudinal extent of the bore, the mirror resides within the body coil imaging region, and the projector resides outside of the body coil imaging region.

9. The system according to claim 8 wherein the mirror is supported by the head coil.

10. The system according to claim 1 wherein the gantry is a magnetic resonance imaging gantry.

11. The system according to claim 10 wherein the projector is magnetic-resonance-imaging-compatible, such that the projector is positionable within the magnetic resonance imaging gantry during magnetic resonance imaging.

12. The system according to claim 11 wherein one or more electronic circuits of the projector are absent of ferrite-core inductors.

13. The display system according to claim 1 wherein at least one optical element is supported relative to said projector such that a magnified virtual image is perceived by the patient at a depth that resides beyond a surface of said magnetic resonance imaging gantry.

14. The system according to claim 1 further comprising control circuitry operably connected to the projector, wherein the control circuitry is configured to deliver, to the projector, position-dependent video content that is dependent on a detected or inferred position of the table relative to the magnetic resonance imaging gantry as the patient is translated toward the magnetic resonance imaging gantry prior to performing a medical imaging or therapeutic procedure.

15. The system according to claim 14 wherein the position-dependent video content delivered to the projector is provided to promote relaxation of the patient as the patient is translated toward the magnetic resonance imaging gantry.

16. The system according to claim 1 wherein the projection screen is a rear projection screen.

17. The system according to claim 1 wherein the projector is battery powered.

18. The system according to claim 1 wherein the projector is operably connected to a wireless receiver for receiving video content.

19. The system according to claim 1 further comprising an optical motion tracking subsystem, the optical motion tracking subsystem comprising at least one motion tracking camera for tracking the position of a fiducial associated with the patient.

20. The system according to claim 19 wherein the at least one motion tracking camera is positioned such that a beam path associated with detection of the fiducial includes reflection from the mirror.

21. A method of displaying images to a patient prior to or during a magnetic resonance imaging procedure involving a magnetic resonance imaging system, the magnetic resonance imaging system comprising:
  a magnetic resonance imaging gantry having an inner bore;
  a table translatable relative to the magnetic resonance imaging gantry;
  a projector;
  a projection screen, wherein the projection screen is positioned, relative to the projector, to provide a display surface for images projected by the projector; and
  a mirror supported relative to the projection screen such that the images projected onto the projection screen are viewable through the mirror by the patient when the patient is residing on the table;
  wherein the projector, the mirror and the projection screen are supported relative to the table such that they move in unison with the table while maintaining a fixed spatial relationship therebetween, and such that images projected by the projector onto the projection screen during translation of the table are projected with a constant projected image field size, thereby reducing a perception of motion by the patient as the patient is translated relative to the magnetic resonance imaging gantry;
  the method comprising:
    during imaging, positioning the mirror, the projector and the projection screen within the bore of the magnetic resonance imaging gantry such that (i) the mirror resides within a body coil imaging region of the magnetic resonance imaging gantry and (ii) the projector resides outside the body coil imaging region without extending beyond an end of the magnetic resonance imaging gantry.

* * * * *